(12) United States Patent
Mellor et al.

(10) Patent No.: US 7,763,251 B2
(45) Date of Patent: Jul. 27, 2010

(54) KITS TO ASSESS THE RISK OF TUMOR PROGRESSION

(75) Inventors: Andrew L. Mellor, Augusta, GA (US); David H. Munn, Augusta, GA (US); Jeffrey Roberts Lee, Martinez, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 687 days.

(21) Appl. No.: 11/474,144

(22) Filed: Jun. 23, 2006

(65) Prior Publication Data

US 2007/0048769 A1     Mar. 1, 2007

Related U.S. Application Data

(62) Division of application No. 10/121,909, filed on Apr. 12, 2002, now abandoned.

(51) Int. Cl.
A61K 39/395     (2006.01)
C07K 16/00     (2006.01)

(52) U.S. Cl. ................... 424/153.1; 530/389.6

(58) Field of Classification Search .................. None
See application file for complete search history.

(56) References Cited

U.S. PATENT DOCUMENTS

| | | | |
|---|---|---|---|
| 4,208,479 A * | 6/1980 | Zuk et al. | ............. 435/7.9 |
| 5,582,831 A | 12/1996 | Shinitzky | |
| 5,648,219 A | 7/1997 | MacKay et al. | |
| 5,849,589 A | 12/1998 | Tedder et al. | |
| 5,851,756 A | 12/1998 | Steinman et al. | |
| 5,871,728 A | 2/1999 | Thomson et al. | |
| 5,994,126 A | 11/1999 | Steinman et al. | |
| 6,008,004 A | 12/1999 | Olweus et al. | |
| 6,080,409 A | 6/2000 | Laus et al. | |
| 6,194,204 B1 | 2/2001 | Crawford et al. | |
| 6,210,662 B1 | 4/2001 | Laus et al. | |
| 6,224,859 B1 | 5/2001 | Thomson et al. | |
| 6,228,640 B1 | 5/2001 | Cezayirli et al. | |
| 6,274,378 B1 | 8/2001 | Steinman et al. | |
| 6,290,972 B1 | 9/2001 | Armitage et al. | |
| 6,303,323 B1 | 10/2001 | Laskey et al. | |
| 6,395,876 B1 | 5/2002 | Munn et al. | |
| 6,451,840 B1 | 9/2002 | Munn et al. | |
| 6,645,491 B1 | 11/2003 | Oldham et al. | |
| 6,734,014 B1 * | 5/2004 | Hwu et al. | ............. 435/325 |
| 2001/0001040 A1 | 5/2001 | Munn et al. | |
| 2002/0138860 A1 | 9/2002 | Cook et al. | |
| 2003/0077247 A1 | 4/2003 | Caux et al. | |
| 2004/0042998 A1 | 3/2004 | Oldham et al. | |
| 2004/0161425 A1 | 8/2004 | Munn et al. | |

FOREIGN PATENT DOCUMENTS

| | | |
|---|---|---|
| WO | WO 92/02637 | 2/1992 |
| WO | WO 99/29310 | 6/1999 |
| WO | WO 00/66764 | 11/2000 |

OTHER PUBLICATIONS

Takikawa, O., et al. Exp. Eye Res. 2001;72:271-277.*
Bjorck, P., "Isolation and Characterization of Plasmacytoid Densritic Cells from Flt3 Ligand and Granulocyte-Macrophage Colony-Stimulating Factor-Treated Mice," Blood, vol. 98, No. 13, pp. 3520-3526, 2001.
Mellor, A. et al., "Ido Expression by Dendritic Cells: Tolerance and Tryptophan Catabolism," Nature, vol. 4, pp. 762-774, 2004.
Pacanowski, J. et al., "Reduced Blood CD123+ (lymphoid) and CD11c+ (myeloid) Dendritic Cell Numbers in Primary HIV-1 infection," Blood, vol. 98, No. 10, pp. 3016-3021, 2001.
Albert, M. L., Dendritic cell maturation is required for the cross-tolerization of $CD8^+$ T cells, Nature Immunol., 2, 1010-1017, 2001.
Alexander, A. M. et al., Indoleamine 2,3-Dioxygenase expressing in transplanted NOD islets prolongs graft survival after adoptive transfer of diabetogenic splenocytes, Diabetes, 51:356-365, 2002.
Baban, B. et al., A Minor Population of Splenic Dendritic Cells Expressing CD19 Mediates IDO-Dependent T Cell Suppression Via Type 1 IFN Signaling Following B7 Ligation. International Immunology, 2005, vol. 17, No. 7, 909-919.
Banchereau, J. et al., Immune and clinical responses in patients with metastatic melonoma to $CD34^+$ progenitor-derived dendritic cell vaccine, Cancer Res., 61, 6451-6458, 2001.
Bell, D. et al., In breast carcinoma tissue, immature dendritic cells reside within the tumor, whereas mature denditric cells are located in peritumoral areas, J. Exp. Med., 190, 1417-1426, 1999.
Bennett, S. R. et al., Help for cytotoxic-T-cell responses is mediated by CD40 signalling, Nature, 393, 478-480, 1998.
Blankenstein, T. et al., Cross-priming versus cross-tolerance: are two signals enough?, Trends in Immunol.,23,171-173, 2002.
Borras, F.E. et al., Identification of Both Myeloid $CD11c^+$ and Lymphoid CD11c Dendritic Cell Subsets in Cord Blood. British Journal of Haematology, 2001, vol. 113, 925-931.

(Continued)

Primary Examiner—G. R Ewoldt
(74) Attorney, Agent, or Firm—Kilpatrick Stockton LLP

(57) ABSTRACT

The present invention is based on the discovery antigen-presenting cells (APCs) may be generated to have predetermined levels of expression of the intracellular enzyme, indoleamine 2,3-dioxygenase (IDO). Because expression of high levels of IDO is correlated with a reduced ability to stimulate T cell responses and an enhanced ability to induce immunologic tolerance, APCs having high levels of IDO may be used to increase tolerance in the immune system, as for example in transplant therapy or treatment of autoimmune disorders. Also disclosed are kits for assessing the relative risk of tumor progression in a subject. For example, disclosed are kits for assessing the relative risk of tumor progression in a subject and having reagents for detection of the enzyme indoleamine 2,3-dioxygenase (IDO) in a sample of tissue from a tumor or tumor draining lymph node from a subject, wherein the reagents are packaged in at least one individual container. The kits may include reagents for detection of cell surface or immunohistochemical markers associated with high IDO expression by APCs such as DO, CD123, CD11c or CCR6.

3 Claims, 9 Drawing Sheets
(1 of 9 Drawing Sheet(s) Filed in Color)

OTHER PUBLICATIONS

Cady, S. G. et al., 1-Methyl-DL-tryptophan, β-(3-Benzofuranyl)-DL-alanine (the Oxygen Analog of Tryptophan), and β-[3-Benzo(b)thienyl]-DL-alanine (the Sulfur Analog of Tryptophan) are competitive inhibitors of Indoleamine 2,3-Dioxygenase, *Arch. Biochem. Biophys.*, 291, 326-333, 1991.

Cella, M. et al., Ligation of CD40 on dendritic cells triggers production of high levels of interleukin-12 and enhances T cell stimulatory capacity:T-T help via APC activiation, *J. Exp. Med.*, 184, 747-752, 1996.

Cella, M. et al., Plasmacytoid monocytes migrate to inflamed lymph nodes and produce large amounts of type I interferon, *Nature Medicine*, 5, 919-923, 1999.

Chen, W. et al., TGF-β released by apoptotic T cells contributes to an immunosuppressive milieu, *Immunity*, 14, 715-725, 2001.

Cobbold, S. et al., Infectious tolerance, *Curr. Opin. Immunol.*, 10, 518-524, 1998.

Curiel, T. J. et al., Tumor immunotherapy: inching toward the finish line, *J. Clin. Invest.*, 109, 311-312, 2002.

Dagher, R. et al., Pilot Trial of Tumor-Specific Peptide Vaccination and Continuous Infusion Interleukin-2 in Patients with Recurrent Ewing Sarcoma and Alveolar Rhabdomyosarcoma: An Inter-Institute NIH Study. Med. Pediatr. Oncol., 2002, vol. 38, 158-164.

Dhodapkar, M. V. et al., Mature Dendritic Cells Boost Functionally Superior CD8+ T-Cell in Humans without Foreign Helper Epitopes, Journal of Clin. Invest., vol. 105, p. R9-R14, 2000.

Dhodapkar, M. V. et al., Antigen-specific inhibition of effector T cell function in humans after injection of immature dendritic cells, *J. Exp. Med.*, 193, 233-238, 2001.

Doan, T. et al., Peripheral tolerance to human papillomavirus E7 oncoprotein occurs by cross-tolerization, is largely Th-2-independent, and is broken by dendritic cell immunization, *Cancer Res.*, 60, 2810-2815, 2000.

Dong et al., B7-H1, a third member of the B7 family, co-stimulates T-cell proliferation and interleukin-10 secretion, *Nature Med.*, 5, 1365-1369, 1999.

Dzionek, A. et al., BDCA-2, BDCA-3, and BDCA-4: Three markers fordistinct subsets of dendritic cells in human peripheral blood, *J. Immunol.*, 165, 6037-6046, 2000.

Facchetti, F. et al., Plasmacytoid monocytes (so-called plasmacytoid T cells) in Hodgkin's disease, *J. Pathol.*, 158, 57-65, 1989.

Fallarino, F et al., Functional expression of indoleamine 2,3-dioxygenase by murine CD8a$^+$, *Inemat Immunol.*, 14(1), 65-68, 2002.

Fiocchi, C., TGF-β/Smad signaling defects in inflammatory bowel disease: mechanisms and possible novel therapies for chronic inflammation, *J. Clin. Invest.*, 108, 523-526, 2001.

Friberg, M. et al., Indoleamine 2,3-Dioxygenase Contributes to Tumor Cell Evasion of T Cell-Mediated Rejection. Int. J. Cancer, 2002, vol. 101, 151-155.

Gallucci, S. et al., Natural adjuvants: Endogenous activators of dendritic cells, *Nat. Med.*, 5, 1249-1255, 1999.

Gorczynski, R. et al., Dendritic cells expressing TGFβ/IL-10, and CHO cells with OX-2 increase graft survival, *Transplantation Proceedings*, 33, 1565-1566, 2001.

Grohmann, U. et al., IL-6 inhibits the tolerogenic function of CD8a$^+$ dendritic cells expressing indoleamine 2,3-dioxygenase, *J. Immunol.*, 167, 708-714, 2001.

Grohmann, U. et al., IFN-ÿ Inhibits Presentation of a Tumor/Self Peptide by CD8ÿ$^-$ Dendritic Cells Via Potentiation of the CD8ÿ$^+$ Subset. *Journal of Immunology*, vol. 165, No. 3, 2000, 1357-1363.

Grouard, G. et al., The enigmatic plasmacytoid T cells develop into dendritic cells with interleukin (IL)-3 and CD40-ligand, *J. Exp. Med.*, 185, 1101-1111, 1997.

Heiser, A. et al., Autologous dendritic cells transfected with prostate-specific antigen RNA stimulate CTL responses against metastatic prostate tumors, *J. Clin. Invest.*, 109, 409-417, 2002.

Honey, K. et al., Dominant regulation: a common mechanism of monoclonal antibody induced tolerance?, *Immunol. Res.*, 20, 1-14, 1999.

Horuzsko, A. et al., Maturation of antigen presenting cells is compromised in HLA-G transgenic mice, *Internet Immunol.*, 13, 385-394, 2001.

Hwu, P. et al., Indoleamine 2,3-Dioxygenase production by human dendrtic cells results in the inhibition of T cell proliferation, *J. Immunol.*, 164:3596-3599, 2000.

Iwasaki, A. et al., Localization of distinct peyer's patch dendritic cell subsets and their recruitment by chemokines macrophage inflammatory protein (MIP)-3α, MIP-3β, and secondary lymphoid organ chemokine, *J. Exp. Med.*, 191, 1381-1393, 2000.

Jonuleit, H. et al., Pro-inflammatory cytokines and prostaglandins induce maturation of potent immunostimulatory dendritic cells under fetal calf serum-free conditions, *Eur. J. Immunol.*, 27, 3135-3142, 1997.

Jonuleit, H. et al., Dendritic cells as a tool to induce anergic and regulatory T cells, *Trends Immunol.*, 22, 394-400, 2001.

Kikuchi, T. et al., Dendritic Cells Modified to Express CD40 Ligand Elicit Therapeutic Immunity against Preexisting Murine Tumors, Blood, vol. 96, No. 1, pp. 91-99, 2000.

Kourilsky, P. et al., Cytokine fields and the polarization of the immune response, *Trends in Immunol.*, 22, 502-509, 2001.

Kudo, Y. et al., Human placental indoleamine 2,3-dioxygenase: cellular location and characterization of an enzyme preventing fetal rejection, *Biochem, Biophys. Acta*, 1500, 119-124, 2000.

Lee, J.R. et al., Pattern of Recruitment of Immunoregulatory Antigen-Presenting Cells in Malignant Melanoma. Laboratory Investigation, 2003, vol. 83, No. 10, 1457-1466.

Liu, Y. J., Dendritic cell subsets and lineages, and their functions in innate and adaptive immunity, *Cell*, 106, 259-262, 2001.

Maloy, K. G. et al., Regulatory T cells in the control of immune pathology, *Nature Immunol.*, 2, 816-822, 2001.

Mellor, A. et al., Extinguishing Maternal Immune Responses during Pregnancy: Implications for Immunosuppression. Seminars in Immunology, vol. 13, No. 4, 2001, 213-218.

Mellor, A. L. et al., Tryptophan catabolism and T cell tolerance: immunosuppression by starvation?, *Immunology Today*, 20, 469-473, 1999.

Mellor, A. L. et al., Tryptophan catabolism prevents maternal T cells from activating lethal anti-fetal immune responses, *J Reprod Immunol*, 52(1-2):5-13, 2001.

Mellor, A. L. et al., HLA-G transgenic mice, *J Reprod Immunol.*, 43, 253-261, 1999.

Mellor, A. L. et al., Immunology at the maternal-fetal interface, *Ann Rev Immunol.*, 18, 367-391, 2000.

Mellor, A. L. et al., Prevention of T cell-driven complement activation and inflammation by tryptophan catabolism during pregnancy, *Nat. Immunol.*, 2, 64-68, 2001.

Mellor, A. L. et al., Cells expressing indoleamine 2,3-dioxygenase inhibit T cell responses, *J. Immunol.*, 168, 3771-3776, 2002.

Miki, T. et al., Blockade of tryptophan catabolism prevents spontaneous tolerogenicity of liver allografts, *Transplantation Proceedings*, 33, 129-130, 2000.

Morita, Y. et al., Dendritic cells genetically engineered to express IL-4 inhibit murine collagen-induced arthritis, *J. Clin. Invest.*, 107, 1275-1284, 2001.

Morse, M.A. et al., Technology evaluation: Theratope, Biomira Inc., *Curr. Opin. Mol. Ther.*, Aug. 2(4):453-458, 2000.

Morse, M. A. et al., Clinical applications of dendritic cell vaccines, *Current Opinion in Molecular Therapeutics*, 2(1):20-28, 2000.

Munn, D. H. et al., Prevention of allogeneic fetal rejection by tryptophan catabolism, *Science*, 281, 1191-1193, 1998.

Munn, D. H. et al., Inhibition of T cell proliferation by macrophange tryptophan catabolism, *J. Exp. Med.*, 189, 1363-1372, 1999.

Munn, D.H. et al., Potential Regulatory Function of Human Dendritic Cells Expressing Indoleamine 2,3-Dioxygenase. Science, 2002, vol. 297, 1867-1870.

Munn, D.H., Tolerogenic Antigen-Presenting Cells. Ann. N.Y. Acad. Sci., 2002, vol. 961, 343-345.

Munn, D.H. et al., Ligation of B7-1/B7-2 by Human CD4$^+$ T Cells Triggers Indoleamine 2,3-Dioxygenase Activity in Dendritic Cells. Journal of Immunology, 2004, vol. 172, 4100-4110.

Munn, D.H. et al., Expression of Indoleamine 2,3-Dioxygenase by Plasmacytoid Dendritic Cells in Tumor-Draining Lymph Nodes. Journal of Clinical Investigation, 2004, vol. 114, No. 2, 280-290.

Munn, D.H. et al., GCN2 Kinase in T Cells Mediates Proliferative Arrest and Anergy Induction in Response to Indoleamine 2,3-Dioxygenase. Immunity, 2005, vol. 22, 633-642.

Munn, D. H. et al., Dendritic Cells Have the Option to Express IDO_Mediated Suppression or Not, Blood, vol. 105, No. 6, p. 2618, 2005.

Nair, S. K. et al., Induction of carcinoembroyonic antigen (CEA)-specific cytotoxic T-lymphocyte responses in vitro using autologous dendritic cells loaded with CEA peptide or CEA RNA in patients with metastic malignancies expressing CEA, *Int. J. Cancer*, 82, 121-124, 1999.

Ochsenbein, A. F. et al., Roles of tumour localization, second signals and cross priming in cytotoxic T-cell induction, *Nature*, 411, 1058-1064, 2001.

Olweus, J. et al., Dendritic cell ontogeny: A human dendritic cell lineage of myeloid origin, *Proc. Natl. Acad. Sci. USA*, 94, 12551-12556, 1997.

Osugi, Y. et al., Myeloid Blood CD11c+ Dendritic Cells and Monocyte-Derived Cells Differ in their Ability to Stimulate T Lymphocytes. Blood, 2002, vol. 100, No. 8, 2858-2866.

Pickl, W. F. et al., Molecular and functional characteristics of dendritic cells generated from highly purified $CD14^+$ peripheral blood monocytes, *J. Immunol.*, 157, 3850-3859, 1996.

Poluektova, L. Y. et al., Generation of cytotoxic T cells against virus-infected human brain macrophages in a urine model of HIV-1 encephalitis, *J Immunol.*, 168:3941-3949, 2002.

Potula, R. et al., Inhibition of Indoleamine 2,3-Dioxygenase (IDO) Enhances Elimination of Virus-Infected Macrophages in an Animal Model of HIV-1 Encephalitis. Blood, 2005, vol. 106, No. 7, 2382-2390.

Reddy, A. et al., A monocyte conditioned medium is more effective than defined cytokines in mediating the terminal maturation of human dendritic cells, *Blood*, 90, 3640-3646, 1997.

Ridge, J. P. et al., A conditioned dendritic cell can be a temporal bridge between a $CD4^+$ T-helper and a T-killer cell, *Nature*, 393, 474-478, 1998.

Roncarolo, M. G. et al., Differentiation of T regulatory cells by immature dendritic cells, *J. Exp. Med.*, 193, F5-F9, 2001.

Sakaguchi, S., Regulatory T cells: key controllers of immunologic self-tolerance, *Cell*, 101, 455-459, 2000.

Schoenberger, S. P. et al., T-cell help for cytotoxic T lymphocytes is mediated by CD40-CD40L interations, *Nature*, 393, 480-483, 1998.

Shevach, E. M., Certified professionals: CD4+CD25+ suppressor T cells, *J. Exp. Med.*, 193, F41-F45, 2001.

Shortman, K. et al., Immunity or tolerance? That is the question for dendritic cells, *Nature Immunol.*, 2, 988-989, 2001.

Shortman, K. et al., Mouse and human dendritic cell subtypes, *Nature Reviews: Immunology*, 2, 151-161, 2002.

Smyth, M. J., et al., A fresh look at tumor immunosurveillance and immunotherapy, *Nature*, 2, 293, 2001.

Sotomayer, E. J. et al., Cross-presentation of tumor antigens by bone marrow-derived antigen-presenting cells is the dominant mechanism in the induction of T-cell tolerance during B-call lymphoma progression, *Blood*, 98, 1070-1077, 2001.

Sozzani, S. et al., The role of chemokines in the regulation of dendritic cell trafficking, *J. Leukocyte Biol.*, 66, 1-9, 1999.

Staveley-O'Carroll, K. et al., Induction of antigen-specific T cell anergy: An early event in the course of tumor progression, *Proc. Natl. Acad. Sci. USA*, 95, 1178-1183, 1998.

Summers, K. L. et al., Phenotypic characterization of five dendritic cell subsets in human tonsils, *Am. J. Pathol.*, 159, 285-295, 2001.

Sutmuller, R. P. M. et al., Synergism of cytotoxic T lymphocyte-associated antigen 4 blockade and depletion of $CD25^+$ regulatory T cells in antitumor therapy reveals alternative pathways for suppression of autoreactive cytotoxic T lymphocyte responses, *J. Exp. Med.*, 194, 823-832, 2001.

Szabolcs, P. et al., Dendritic cells and macrophages can mature independently from a human bone marrow-derived, post-colony-forming unit intermediate, *Blood*, 87, 4520-4530, 1996.

Taylor, M. W. et al., Relationship between interferon-γ, indoleamine 2,3-dioxygenase, and tryptophan catabolism, *FASEB J.*, 5, 2516-2522, 1991.

Tan, P.H. et al., Creation of Tolerogenic Human Dendritic Cells via Intercellular CTLA4: A Novel Strategy with Potential in Clinical Immunosuppression, Blood, vol. 106, No. 9, pp. 2936-2943, 2005.

Tan, P.H. et al., Modulation of Human Dendritic Cell Function following Transduction with Viral Vectors: Implications for Gene Therapy, American Society of Hematology, Blood First Edition Paper, prepublished online Jan. 25, 2005.

Terness, P. et al., Regulation of Human Auto and Alloreactive T Cells by Indoleamine 2,3-Dioxygenase (IDO)-Producing Dendritic Cells: Too Much Ado about IDO? Blood, vol. 105, No. 6, 2005, 2480-2486.

Terness, P. et al., The Immunoregulatory Role of IDO-Producing Dendritic Cells Revisited, Trends in Immunology, vol. 27, pp. 68-73, 2006.

Thompson, A. W. et al., Are dendritic cells the key to liver transplant tolerance:, *Immunol. Today*, 20, 27-31, 1999.

Van Elsas, A. et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastic tumors accompanied by autoimmune depigmentation, *J. Exp. Med.*, 190, 355-366, 199.

Van Elsas, A. et al., Elucidating the autoimmune and antitumor effector mechanisms of a treatment based on cytotoxic T lymphocyte antigen-4 blockade in combintion with a B16 melonoma vaccine: comparison of prophylaxis and therapy, *J. Exp. Med.*, 194, 481-489, 2001.

Varona, R. et al., CCR6-deficient mice have impaired leukocyte homeostasis and altered contact hypersensitivity and delayed-type hypersensitivity responses, *J. Clin. Invest.*, 107, R37-R45, 2001.

Waldmann, H. et al., Regulating the immune response to transplants: a role for $CD4^+$ regulatory cells?, *Immunity*, 14, 399-406, 2001.

Yang, D. et al., Cuytting edge: Immature dendritic cells generated from monocytes in the presence of TGF-β1 express functional C-C chemokine receptor 6, *J. Immunol.*, 163, 1737-1741, 1999.

Yoon, J.-W. et al., Control of autoimmune diabetes in NOD mice by GAD expression or suppression of β cells, *Science*, 284, 1183-1187, 1999.

Yoshida, R. et al., Tryptophan Degradation in Transplanted Tumor Cells Undergoing Rejection, Journal of Immunology, vol. 141, No. 8, pp. 2819-2823, 1998.

Zlotnik, A. et al., Chemokines: a new classification system and their role in immunity, *Immunity*, 12, 121-127, 2000.

Chapman et al., "Pharmacologically active benzo'bithiophene derivatives. VIII Benzo-bithiophene analogs of tryptophan and alpha-methyltryptophan, and some of their 5-substituted derivatives," *Journal of the Chemical Society, Section C: Organic Chemistry*, 1969, (14): 1855-1859 (abstract).

Friberg et al., "Indoleamine 2,3-dioxygenase (IDO) protects established tumors from T cell mediated rejection," *Proc. Amer. Ass. Cancer. Res. Ann. Meet.*, 2000, 41: 112 (abstract).

Frumento et al., "Inhibition of T cell proliferation by the purified enzyme indoleamine 2,3-dioxygenase," *Human Immunology, The European Federation for Immunogenetics 14th Annual Conference*, Apr. 4-7, 2000, 61: S140 (abstract).

Munn et al., "Regulation of T cell activation by macrophage (Mvariant phi)—mediated tryptophan (TRP) depletion," *FASEB Journal*, 1998, 12: A276 (abstract).

Munn et al., "Macrophage inhibition of T cell activiation via depletion of tryptophan," *Blood*, 1997, 90: 448A-449A (abstract).

Peterson et al., "Evaluation of functionalized tryptophan derivatives and related compounds as competitive inhibitors of indoleamine 2,3-dioxygenase," *Medicinal Chemistry Research*, 1994, 3(8): 531-544 (abstract).

Southan et al., "Structural requirements of the competitive binding site of recombinant human indoleamine 2,3-dioxygenase," *Medicinal Chemistry Research*, 1996, 6(5): 343-352 (abstract).

Lob, S. et al., "Levo-but not dextro-1-methyl tryptophan abrogates the IDO activity of human dendritic cells," Blood, 111(4):2152-2154, 2008.

Brandacher, G. et al., Prognostic Value of Indoleamine 2,3-Dioxygenase Expression in Colorectal Cancer: Effect on Tumor-Infiltrating T Cells, Clin Cancer Res., vol. 12(4), pp. 1144-1151, 2006.

Grant et al., Induction of Indolamine 2,3-Dioxygenase in Primary Human Macrophages by Human Immunodeficiency Virus Type 1 is Strain Dependent, J. of Virology, 74(9), pp. 4110-4115, 2000.

Hansen et al., Tissue Distribution of Indoleamine 2,3-Dioxygenase in Normal and Malaria Tissue, Redox Rep., vol. 5(2-3), pp. 112-115, 2000.

Munn, D. et al., Expression of Indoleamine 2,3-Dioxygenase by Plasmacytoid Dendritic Cells in Tumor-Draining Lymph Nodes, J. Clin. Invest., vol. 114(2), pp. 280-290, 2004.

Okamoto et al., Indoleamine 2,3-Dioxygenase Serves as a Marker of Poor Prognosis in Gene Expression Profiles of Serous Ovarian Cancer Cells, Clin Cancer Res, vol. 11(16), pp. 6030-6039, 2005.

Sedlmayr et al., Localization of Indoleamine 2,3-dioxygenase in Human Female Reproductive Organs and the Placenta, Mol Hum Reprod., vol. 8(4), pp. 385-391, 2002.

Takikawa et al., "Indoleamine 2,3-dioxygenase in the Human Lens, the First Enzyme in the Synthesis of UV Filters," Exp. Eye Res., vol. 72, pp. 271-277, 2001.

Written Decision and Minutes of Oral Proceedings of Nov. 17, 2009 for corresponding European Patent Application No. 02807233.8. Authors: Sommerfeld et al., Date: Jan. 12, 2009.

* cited by examiner

Positively-selected (CD123+) DCs

Upper limit of negative control for IDO (neutralized primary antibody)

Negatively selected (post-sort, CD123-depleted) DCs

KITS TO ASSESS THE RISK OF TUMOR PROGRESSION

This application is a divisional of U.S. patent application Ser. No. 10/121,909, filed Apr. 12, 2002 now abandoned.

The studies described herein were supported at least in part by Federal grants from the National Institutes of Health (NIH R01 HL60137; NIH R01 HL57930; NIH R01 AI44219; NIH R21 AI49849; NIH R21 AI44759; and NIH K08 HL03395), the National Institutes of Health and National Cancer Institute (NIH/NCI/RAID) and the Mason Trust Foundation. Thus, the Federal government may have rights in this invention.

FIELD OF THE INVENTION

The invention relates to the use of cell-based pharmaceuticals, and more specifically, to the use of antigen-presenting cells (APCs) selected as comprising immunosuppressive APCs for inducing tolerance, or immunostimulatory APCs for inducing an increased immune response. As examples, immunosuppressive APCs may be used as transplant therapeutics, whereas preparations of immunostimulatory APCs may be used as anti-cancer or anti-viral vaccines.

BACKGROUND OF THE INVENTION

Once established, human tumors are not rejected by the immune system, a state of functional tolerance which eventually proves fatal to the host (Smyth, M. J., et al., *Nat. Immunol.* 2, 293 (2001)). Evidence from murine models suggests that immunologic unresponsiveness may arise when tumor-associated antigens are presented by certain bone marrow-derived tolerogenic (tolerance-producing) antigen-presenting cells (APCs) (Sotomayor, E. M., et al., *Blood,* 98: 1070-1077 (2001); Doan, T., et al., *Cancer Res.,* 60: 2810-2815 (2000)). In the setting of tissue transplantation, it would be desirable to isolate and administer such tolerogenic APCs. However, in humans and other mammals (other than mice), the identity of these APCs, and the mechanisms they use to induce tolerance, remain elusive.

In humans, "immature" myeloid dendritic cells (DCs) have been postulated to function as tolerizing APCs based on findings that these cells: (1) have a decreased ability to stimulate T cell responses in vitro (Reddy, A., et al., *Blood,* 90: 3640-3646 (1997); Jonuleit, H., et al., *Eur. J. Immunol.,* 27: 3135-3142 (1997)); (2) may promote the function of immunosuppressive or "regulatory" T cells following prolonged co-incubation (Jonuleit, H., et al., *Trends Immunol.,* 22: 394-400 (2001)); and (3) have the ability to abrogate antigen-specific T cell responses in vivo (Dhodapkar, M. V., et al., *J. Exp. Med.,* 193: 233-238 (2001); see also U.S. Pat. Nos. 5,871,728 and 6,224,859). However, the molecular mechanism used by immature DCs or other putative tolerogenic APCs to suppress T cell responses is unclear. Moreover, there is currently no way to identify or isolate tolerogenic APCs in vitro or in vivo, and thus, their use as therapeutic agents is still not available for most applications.

More fundamentally, the supposition that immature DCs are tolerogenic is based on an unproven and potentially flawed model of how APCs regulate T cell activation. Thus, a prevailing model teaches that T cells are rendered unresponsive (or "tolerized") when they receive an activation signal (signal 1) via the T cell antigen receptor (TCR) without receiving co-stimulatory signals (e.g. from CD80 and CD86) delivered on APCs (signal 2). Immature DCs express low levels of TCR ligands (such as MHC class II antigens) and low levels of the putative costimulatory molecules. Thus, the model teaches that immature of DCs are unable to activate T cells because T cells receive signal 1 without adequate signal 2.

Other findings teach against the prevailing model, and indicate that maturation of DCs is not necessarily associated with abrogation of T cell suppression and/or tolerance (Albert, M. L., *Nature Immunol.,* 2: 1010 (2001); Shortman, K. et al., *Nature Immunol.,* 2: 988-989 (2001); T. Bankenstein and T. Schuler, *Trends in Immunol.,* 23: 171-173 (2002)). Instead, there may be a third, as yet undefined signal (signal 3) that acts after T cells have received the signals of antigen presentation and co-stimulation (i.e. signals 1 and 2) from a fully mature APC. The third signal then diverts T cells to activation or tolerance. In this model, the tolerogenic phenotype is independent of the maturation status of the APC (in fact, maturation enhances tolerance induction) and depends instead on an intrinsic attribute of the APC (i.e. whether it expresses signal 3).

The inventors believe that most DC preparations are in fact mixtures of immunizing (stimulatory) and tolerizing APCs. The presence of a mixed population of DCs in such preparations would explain why therapeutic immunization in cancer patients using DCs remains problematic, with most studies having only limited success (M. A. Morse and H. K. Lyerly, *Curr. Opin. Mol. Ther.,* 2: 20 (2000)). For example, the preferred source and differentiation status of DCs for clinical use remains controversial (Curiel T. J., and Curiel, D. T., *J. Clin. Invest.,* 109: 311-312, 2002). Although development of the field has been assisted by the recognition that the maturation state of human DCs plays an important role in their ability to stimulate effective immunity (Dhodapkar, M. V., et al., *J. Clin. Invest.,* 105: R9-R14 (2000); Dhodapkar, M. V., et al., *J. Exp. Med.,* 193: 233-238 (2001)), even using the best isolation and maturation strategies and multiple tumor antigens, clinically useful therapeutic immunization in patients with established tumors has been only partially effective (Banchereau, J., et al., *Cancer Res.,* 61: 6451-6458 (2001)). Thus, it would be useful to develop methods to isolate DCs which, rather than being a mixed population of activating and suppressive DCs, comprise pure activating DCs.

Conversely, these are some situations where increased tolerance to foreign antigens is desired. In one approach, immature dendritic cells (DCs) uncharacterized as suppressive or immunogenic subsets are propagated in the presence of a cytokine regimen to maintain the cells in an immature state. The immature cells are administered to a host in advance of a transplant to enhance tolerance (U.S. Pat. Nos. 5,871,728 and 6,224,859). However, this approach inherently sacrifices efficient antigen presentation and co-stimulation due to the immaturity of the APCs, and risks delivering unwanted immunizing (non-tolerogenic) DCs as part of the heterogeneous DC population. It would be helpful in transplant therapeutics to be able to create well-characterized populations of mature maximally effective tolerogenic APCs which present the antigen subset of interest, but in a tolerizing (tolerance-promoting) preparation.

What is needed is a way to separate tolerance-inducing APCs from other (non-tolerance-inducing) APCs. The tolerance-inducing APCs can then be used in transplant procedures to promote tolerance to specific donor antigens. The non-tolerance-inducing APCs can be used in conjunction with undesirable foreign antigens (such as tumor antigens) as a vaccine, to prime the recipient immune system against the antigen in question.

SUMMARY OF THE INVENTION

The present invention relies on the discovery that tolerance-inducing (suppressive) antigen-presenting cells (APCs) exhibit high levels of expression of the intracellular enzyme indoleamine-2,3-dioxygenase (IDO), and non-tolerance-inducing (non-suppressive or T-cell activating) APCs exhibit low levels of IDO expression. IDO is both a marker for the suppressive subset, and also the causal mechanism of suppression. Thus, the present invention describes the generation of enriched populations of tolerance-inducing APCs and their use as therapeutics, and the generation of enriched populations of non-suppressive APCs and their use as therapeutics. For example, APCs having high levels of IDO (IDO$^+$), and exposed to antigens from a donor may be used to increase tolerance of a transplant recipient to the donor's tissue by presenting the donor's antigens on tolerance-inducing APCs. Conversely, APCs having low levels of IDO (IDO$^{LO}$) may be used to enhance responses to neo-antigens from tumors and infectious agents.

Thus, in one aspect, the present invention comprises a method of making antigen-presenting cells (APCs) for enhancing T cell tolerance comprising the steps of:

(a) isolating antigen-presenting cells (APCs) or their precursors (APC progenitors) from a first subject; and (b) treating the cells to select for tolerance-inducing APCs expressing levels of indoleamine 2,3-dioxygenase (IDO) enzyme activity sufficient to suppress proliferation of T cells (IDO$^+$ APCs).

In another aspect, the present invention comprises a method for increasing the number of tolerance-inducing antigen-presenting cells (APCs) in a subject comprising treating the subject to increase the production of antigen-presenting cells (APCs) or their precursors (APC progenitors) expressing levels of indoleamine 2,3-dioxygenase (IDO) enzyme activity sufficient to suppress proliferation of T cells (IDO$^+$ APCs).

In another aspect, the present invention comprises a method for enhancing tolerance in a subject comprising the steps of:

(a) isolating antigen-presenting cells (APCs) or their precursors (APC progenitors) from a first subject;

(b) treating the cells to select for tolerance-inducing APCs expressing levels of indoleamine 2,3-dioxygenase (IDO) enzyme activity sufficient to suppress proliferation of T cells (IDO$^+$ APCs); and (c) administering the treated cells of step (b) to the original subject or to a second subject in an amount effective to generate a tolerance-promoting immune response in the recipient subject.

The present invention also provides compositions for enhancing T cell tolerance comprising APCs that express high levels of indoleamine 2,3-dioxygenase (IDO) enzyme activity (IDO$^+$ APCs). Such tolerizing APCs may be used to promote acceptance of graft or transplant tissue from a donor subject in a recipient. IDO+ APCs may be made by the methods described herein, or by other methods in the art. Thus, in one aspect, the present invention comprises isolated antigen-presenting cells (APCs) selected as comprising APCs expressing levels of indoleamine 2,3-dioxygenase (IDO) enzyme activity sufficient to suppress proliferation of T cells (IDO$^+$ APCs). In another aspect, the present invention comprises an isolated antigen-presenting cell selected as comprising expression of indoleamine 2,3-dioxygenase (IDO) enzyme activity at a level sufficient to suppress proliferation of T cells. In yet another aspect, the present invention comprises antigen-presenting cells comprising expression of indoleamine 2,3-dioxygenase (IDO) enzyme activity at a level sufficient to suppress proliferation of T cells (IDO$^+$ APCs) made by the methods of the present invention.

Alternatively, the present invention describes the generation of immunostimulatory (non-tolerance-inducing) APCs having reduced IDO expression (IDO$^{LO}$ APCs). APCs having reduced levels of IDO expression and exposed to antigens expressed by a tumor or pathogen (such as HIV) may be used as vaccines, by presenting cancer or pathogen antigens on APCs which contain fewer tolerance-inducing APCs.

Thus, in this aspect, the present invention comprises a method of making antigen-presenting cells (APCs) for enhancing T cell dependent immunologic activation in a subject comprising the steps of:

(a) isolating antigen-presenting cells (APCs) or their precursors (APC progenitors) from a subject; and (b) treating the isolated cells to select for APCs expressing levels of indoleamine 2,3-dioxygenase (IDO) enzyme activity not sufficient to cause suppression of T cell proliferation (IDO$^{LO}$ APCs).

In another aspect, the present invention comprises a method for increasing the number of non-suppressive antigen-presenting cells (APCs) in a subject comprising treating said subject to increase the population of antigen-presenting cells (APCs) or their precursors (APC progenitors) expressing levels of indoleamine 2,3-dioxygenase (IDO) enzyme activity not sufficient to cause suppression of T cell proliferation (IDO$^{LO}$ APCs).

In another aspect, the present invention comprises a method for increasing the protective immune response in a subject comprising the steps of:

(a) isolating antigen-presenting cells (APCs) or their precursors (APC progenitors) from a first subject;

(b) treating the isolated cells to select for APCs expressing levels of indoleamine 2,3-dioxygenase (IDO) enzyme activity not sufficient to cause suppression of T cell proliferation (IDO$^{LO}$ APCs); and (c) administering the treated cells from step (b) to the subject in an amount effective to generate a protective immune response in the subject.

The present invention also provides compositions for increasing T cell activation. Such compositions may be used to increase the T cell response to antigens in a subject. In this aspect, the present invention comprises isolated antigen-presenting cells (APCs) selected as comprising APCs expressing levels of indoleamine 2,3-dioxygenase (IDO) enzyme activity not sufficient to cause suppression of T cell proliferation (IDO$^{LO}$ APCs). In another aspect, the present invention comprises an isolated antigen-presenting cell (APC) selected as comprising levels of indoleamine 2,3-dioxygenase (IDO) enzyme activity not sufficient to cause suppression of T cell proliferation. In yet another aspect, the present invention comprises antigen-presenting cells (APCs) comprising levels of indoleamine 2,3-dioxygenase (IDO) enzyme activity not sufficient to cause suppression of T cell proliferation (IDO$^{LO}$ APCs) made by the methods of the present invention.

The present invention also describes methods to quantitate the levels of immunosuppressive APCs in a population of APCs. Thus, in one aspcect, the present invention comprises a method to determine the number of tolerance-inducing antigen-presenting cells (APCs) in a cell population comprising measuring the number of cells expressing levels of indoleamine 2,3-dioxygenase (IDO) enzyme sufficient to suppress proliferation of T cells (IDO⁺ APCs) in the population. In another aspect, the present invention comprises a kit for determining the number of tolerance-inducing antigen-presenting cells (APCs) in a cell population comprising reagents to measure levels of indoleamine 2,3-dioxygenase (IDO) enzyme in the population of APCs, wherein the reagents are packaged in at least one individual container.

The immunosuppressive APCs may also be quantified using a biological assay. Thus, in another aspect, the present invention comprises a method to quantify the ability of a population of cells to suppress T cell proliferation comprising measuring the increase in T cell proliferation in the presence of an IDO inhibitor as compared to in the absence of an IDO inhibitor. The present invention also comprises a kit for determining the ability of a population of antigen-presenting cells to suppress T cell proliferation comprising an IDO inhibitor packaged in at least one individual container.

Additionally, the present invention provides for a diagnostic assay, based on detection of IDO⁺ APCs and/or mip-3α expression in tumors and tumor-draining lymph nodes. In this aspect, the present invention comprises a method for assessing the relative risk of tumor progression in a subject comprising the steps of:

(a) assaying a sample of tissue from a tumor or tumor draining lymph node from a subject for expression of the enzyme indoleamine 2,3-dioxygenase (IDO); and (b) correlating the risk of tumor progression to IDO expression in the tissue sample, wherein IDO expression is positively correlated with an increase in the risk of tumor progression.

The present invention also comprises a method for assessing the risk of tumor progression in a subject comprising the steps of:

(a) assaying a sample of tissue from a tumor or tumor draining lymph nodes from a subject for mip-3α expression; and (b) correlating the risk of tumor progression to mip-3α expression in the tissue sample, wherein mip-3α expression is positively correlated with an increase in the risk of tumor progression.

The present invention also comprises kits for assessing the relative risk of tumor progression in a subject. For example, in one aspect, the present invention comprises a kit for assessing the relative risk of tumor progression in a subject comprising reagents for detection of the enzyme indoleamine 2,3-dioxygenase (IDO) in a sample of tissue from a tumor or tumor draining lymph node from a subject, wherein the reagents are packaged in at least one individual container. In another aspect, the present invention comprises a kit for assessing the relative risk of tumor progression in a subject comprising reagents for detection of relative levels of expression of mip-3α in a sample of tissue from a tumor or tumor draining lymph node from a subject, wherein the reagents are packaged in at least one individual container.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

From the foregoing summary, it is apparent that an object of the present invention is to provide methods and compositions for enriching and isolating IDO⁺ antigen-presenting cells for use in therapeutic applications such as the prevention of transplant rejection. In addition, it is apparent that an object of the present invention is to provide methods and compositions for isolating antigen-presenting cells depleted of IDO⁺ antigen-presenting cells (i.e. IDO$^{LO}$ APCs) comprising reduced suppression or tolerance, as for example in cancer prevention and therapy. These, together with other objects of the present invention, along with various features of novelty which characterize the invention, are pointed out with particularity in the claims and description provided herein.

BRIEF DESCRIPTION OF THE FIGURES

The file of this patent contains at least one drawing executed in color. Copies of this patent or patent application publication with color drawing(s) will be provided by the Office upon request and payment of the necessary fee.

DETAILED DESCRIPTION OF THE INVENTION

Figure 1:
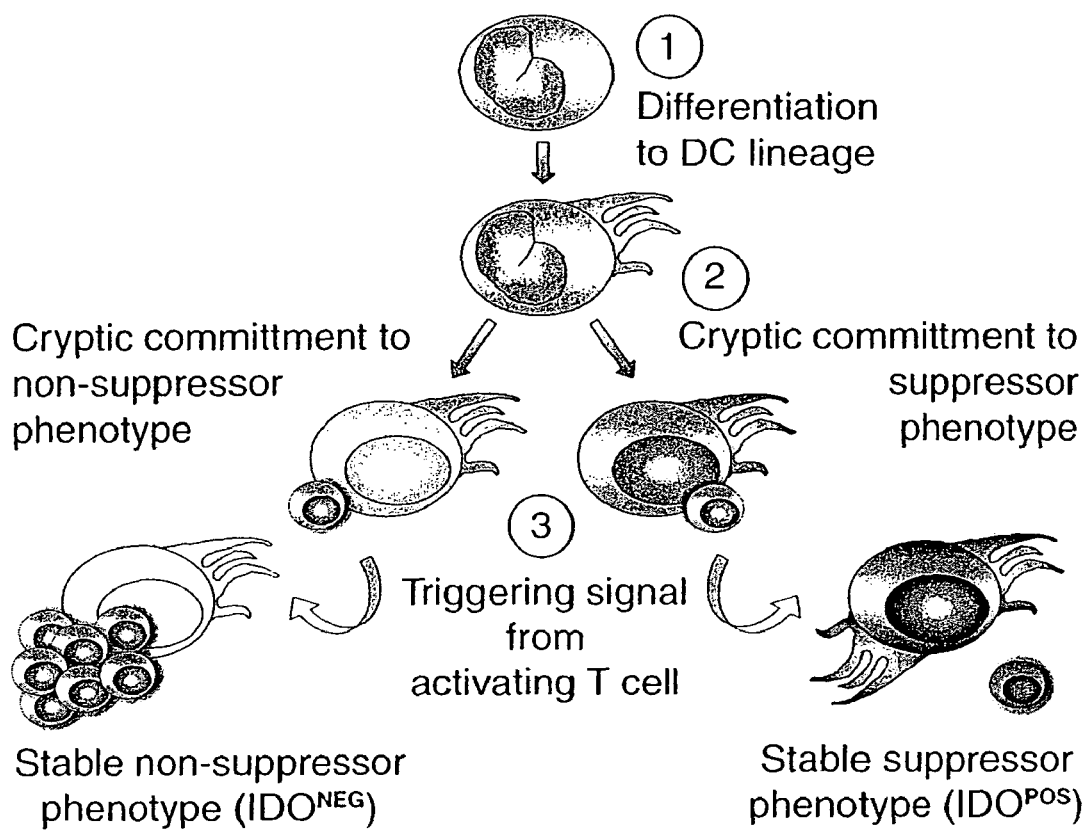
FIG. 1 shows a schematic representation of a 3-step model for the regulation of IDO during dendritic cell (DC) differentiation in accordance with an embodiment of the present invention.

The present invention describes the isolation of myeloid-derived antigen-presenting cells (APCs) which are enriched for tolerance-inducing APCs, or depleted of tolerance-inducing APCs, and the use of these cells for various therapeutic applications. The present invention relies on the discovery that antigen-presenting cells may be separated into a tolerance-inducing population, which is associated with high levels of expression of the enzyme indoleamine-2,3-dioxygenase (IDO), and a T cell activating (non-tolerance-inducing) population, which is associated with low levels of expression of IDO. For example, APCs having high levels of IDO (IDO$^+$ APCs), and constitutively expressing or exposed to donor tissue antigens may be used to increase tolerance of the recipient to the donor's tissue in transplant therapy by presenting the antigens on tolerance-inducing APCs. Alternatively, APCs having reduced levels of IDO expression (IDO$^{LO}$ APCs) and exposed to antigens expressed by cancer tissue or virus may be used as anti-cancer vaccines or anti-viral vaccines, respectively, by presenting the antigens on APCs depleted on tolerance-inducing cells.

Thus, the current invention teaches that conventional preparations of human APCs can contain two independent subsets: an IDO$^+$ subset (comprising relatively high levels of IDO expression); and an IDO$^{LO}$ subset (comprising little to no IDO expression). Moreover, which of these two types of APC predominates is highly (and in some cases unpredictably) dependent on the culture conditions or other variables. In many applications, even a minor contaminating admixture of the undesired type of APC (i.e. IDO$^{LO}$ vs. IDO$^+$) may render the APC population unusable, or even harmful, for the desired application. For example, if the goal is to generate tolerance toward donor histocompatability antigens prior to organ transplantation, exposure to even a minority of activating dendritic cells could promote worsened rejection. Conversely, if the goal is to enhance responses to weak tumor antigens, the presence of even a minor population of IDO+ tolerance-inducing cells may be enough to suppress the desired response (see e.g., Grohmann, U., et al., *J. Immunol.* 167: 708-714 (2001), for studies in murine model).

Thus, in one aspect, the present invention describes a method of making antigen-presenting cells (APCs) for enhancing T cell tolerance comprising the steps of:

(a) isolating antigen-presenting cells (APCs) or their precursors (APC progenitors) from a first subject; and (b) treating the isolated cells to select for tolerance-inducing APCs expressing levels of indoleamine 2,3-dioxygenase (IDO) enzyme activity sufficient to suppress proliferation of T cells (IDO$^+$ APCs).

Preferably, the tolerance-inducing IDO$^+$ APCs comprise at least 90% of the APC population expressing IDO at levels of at least 2-fold over background. More preferably, the tolerance-inducing IDO$^+$ APCs comprise at least 95% of the APC population expressing IDO at levels of at least 2-fold over background.

Alternatively, IDO$^+$ APCs may be quantitated by measuring the biological activity of the preparation. Thus, in an embodiment, the tolerance-inducing IDO$^+$ APCs comprise suppressor activity, comprising an at least a 2-fold increase in T cell proliferation in the presence of an IDO inhibitor as compared to in the absence of an IDO inhibitor. Suppressor activity may be measured using a mixed leukocyte reaction or similar assay of T cell proliferation. Preferably, the IDO inhibitors comprise 1-methyl-(D,L)-tryptophan, β-(3-benzofuranyl)-(D,L)-alanine, β-(3-benzo(b)thienyl)-(D,L)-alanine, or 6-nitro-(D,L)-tryptophan. More preferably, the IDO inhibitors comprise 1-methyl-(D)-tryptophan or 6-nitro-(D)-tryptophan.

In an embodiment, the isolated APCs or APC progenitors comprise mature blood-derived dendritic cells, mature tissue dendritic cells, monocyte-derived macrophages, non-dendritic APCs, B cells, plasma cells, or any mixture thereof. Preferably, the isolated APCs or APC progenitors comprise a cell type bearing markers of antigen presentation and costimulatory function. Also preferably, the APCs or APC progenitors are isolated from peripheral blood, bone marrow, lymph nodes or a solid organ from a human or other mammal.

The treatment to select for $IDO^+$ APCs may comprise predetermined culture conditions or physical selection. Preferably, step (b) comprises culturing the cells in medium which is essentially free of serum. Also preferably, step (b) comprises culturing the cells in the presence of granulocyte-macrophage colony stimulating factor (GMCSF). Step (b) may also comprise culturing the cells in the presence of macrophage colony stimulating factor (MCSF). In addition, step (b) may comprise culturing the cells in the presence of IL4. Step (b) may also comprise culturing the cells in the presence of TGFβ and/or IL10. For example, in an embodiment, a cytokine cocktail such as those known in the art (Jonuleit, H., et al., *Eur. J. Immunol.*, 27: 3135-3142 (1997)) may be employed.

In an embodiment, step (b) also comprises culturing the cells with an agent to cause or regulate maturation of those APCs that express high levels of IDO. Such maturation agents may include, but are not limited to TNFα, IL10, TGFβ, CD40-ligand, activating anti-CD40 antibodies, cells engineered to express cell-surface CD40-ligand, proinflammatory bacterial or pathogen products, or any combination thereof. Thus, for selection of $IDO^+$ APCs these agents may be combined singly, or added together with other agents used for the maturation of DCs (Jonuleit, H., et al., *Eur. J. Immunol.* 27: 315-3142 (1997); Reddy, A., et al., *Blood* 90: 3640-3646 (1997).

In an embodiment, step (b) may comprise genetically modifying the APCs or APC progenitors such that the final preparation comprises APCs expressing levels of indoleamine 2,3-dioxygenase (IDO) enzyme activity sufficient to suppress proliferation of T cells ($IDO^+$ APCs). As an example, transfection of the culture of APCs or APC progenitors with a gene for a cytokine or ligand may be employed (Kikuchi, T., et al., *Blood* 98: 91-99 (2000); Gorckynski, R., et al., *Transplantation Proceedings* 33: 1565-1566 (2001); Morita, Y., et al., *J. Clin. Invest.*, 107: 1275-1284 (2001)).

In an embodiment, the method utilizes cell surface proteins or other markers for separation (enrichment or depletion) of $IDO^+$ cells from other APCs. Thus, in an embodiment, the method includes measuring expression of at least one cell surface marker that identifies the APCs as expressing levels of IDO sufficient to suppress T cell proliferation ($IDO^+$ APCs) or as expressing levels of IDO not sufficient to suppress T cell proliferation ($IDO^{LO}$ APCs). Preferably, the cell surface marker is used to separate $IDO^+$ APCs from $IDO^{LO}$ APCs. The markers used for differential selection of $IDO^+$ cells from $IDO^{LO}$ cells include, but are not limited to, CD123, CD11c, CCR6, CD14 or any combination thereof. Alternatively, the method may include differential adhesion to a substrate to separate APCs that expressing levels of IDO sufficient to suppress T cell proliferation ($IDO^+$ APCs) from APCs expressing levels of IDO not sufficient to suppress T cell proliferation ($IDO^{LO}$ APCs).

One object of the present invention is to develop tolerance-promoting APCs that present a specific subset of antigens of interest. For example, tolerance-promoting ACPs that present antigens from a donor may be administered to a transplant recipient to promote acceptance of a graft or transplant. Thus, in an embodiment, the subject from which the APCs or APC progenitors are isolated comprises a tissue donor to a second subject. In another embodiment, the APCs or APC progenitors are isolated from a subject with an autoimmune disorder for subsequent preparation of $IDO^+$ APCs for use in treating the disorder.

In addition, the treated APCs may be exposed to at least one source of antigen after isolation from a subject and treatment to select for $IDO^+$ APCs. In an embodiment, the antigen comprises a purified, or a synthetic or recombinant polypeptide representing a specific antigen to which it is desired that tolerance be induced, or a short synthetic polypeptide fragment derived from the amino acid sequence of such an antigen. Preferably, the source of antigen comprises antigens expressed by a donor tissue graft. Also preferably, the source of antigen comprises protein or other material to which a patient has an autoimmune disorder (see e.g. Yoon, J.-W., et al., *Science* 284: 1183-1187 (1999) for examples of such proteins). In yet another embodiment, the method comprises transfecting or genetically engineering the $IDO^+$ APCs to express at least one antigenic polypeptide.

The tolerance-inducing APCs or their precursors (or non-tolerance inducing APCs or their precursors) as defined by the methods of the present invention may also be increased in number in a subject by administering to the subject agents that increase the number of the desired APCs. Numerous cytokines and other agents have been shown to increase the number of one or more of different types of APCs when administered in vivo. Examples of such agents include MCSF, GMCSF, granulocyte colony-stimulating factor (GCSF), FLT3-ligand, and other natural and artificial cytokines and hematopoietic growth factors. Previously, however, it was not known whether the APCs induced by such treatments were tolerance-inducing or non-tolerance-inducing or a mixture of both. The present invention provides the discovery that by measuring IDO expression following isolation and in vitro treatment of the desired APC population, the effectiveness of such in vivo treatments can be evaluated and improved upon. In addition, as described herein, the present invention provides methods to quantify IDO expression, both on a cell-by-cell basis and as a biologicial assay for bulk populations. Thus, in an embodiment, tolerogenic APCs or their precursors in peripheral blood from a donor may be increased by treatment with selected cytokines prior to isolation for in vitro culture and delivery to a recipient for the purpose of inducing transplantation tolerance.

Thus, in one aspect, the present invention comprises a method for increasing the number of tolerance-inducing antigen-presenting cells (APCs) in a subject comprising treating the subject to increase the production of APCs or their precursors (APC progenitors) expressing levels of indoleamine 2,3-dioxygenase (IDO) enzyme activity sufficient to suppress proliferation of T cells ($IDO^+$ APCs).

In another aspect, the present invention comprises a method for enhancing tolerance in a subject comprising the steps of:

(a) isolating antigen-presenting cells (APCs) or their precursors (APC progenitors) from a first subject;

(b) treating the cells to select for APCs expressing levels of indoleamine 2,3-dioxygenase (IDO) enzyme activity sufficient to suppress proliferation of T cells ($IDO^+$ APCs); and (c) administering the treated cells of step (b) to the original subject or to a second subject in an amount effective to generate a tolerance-promoting response in said recipient subject.

Preferably, the tolerance-promoting response reduces T cell activation in the recipient subject. Also preferably, the tolerance-promoting response prolongs the survival of transplanted cells or tissues in the recipient subject. Also preferably, the tolerance-promoting response reduces the symptoms of an autoimmune disease in the recipient subject.

In an embodiment, the subject from which the APCs or APC progenitors are isolated comprises a tissue donor to the recipient subject. In another embodiment, the subject from which the APCs or APC progenitors are isolated comprises a mammal with an autoimmune disorder.

The method may include exposing the APCs or APC progenitors to at least one source of antigen after isolation from the first subject and treatment to select for IDO$^+$ APCs. Preferably, the antigen comprises a synthetic or natural polypeptide. Also preferably, the antigen comprises at least one antigen expressed by a donor tissue graft. Alternatively, the antigen may comprise at least one antigen to which the recipient subject has an autoimmune disorder. In another embodiment, the method may comprise transfecting or genetically engineering the APCs selected as IDO$^+$ to express at least one antigenic polypeptide.

The present invention also provides compositions for enhancing T cell tolerance. Such tolerizing APCs may be used to promote acceptance of graft or transplant tissue from a donor subject in a recipient or to treat a patient with autoimmune disease. In this aspect, the present invention comprises isolated antigen-presenting cells (APCs) selected as comprising APCs expressing levels of indoleamine 2,3-dioxygenase (IDO) enzyme activity sufficient to suppress proliferation of T cells (IDO$^+$ APCs). In another aspect, the present invention comprises an isolated antigen-presenting cell selected as comprising expression of indoleamine 2,3-dioxygenase (IDO) enzyme activity at a level sufficient to suppress proliferation of T cells. In yet another aspect, the present invention comprises antigen-presenting cells comprising expression of indoleamine 2,3-dioxygenase (IDO) enzyme activity at a level sufficient to suppress proliferation of T cells (IDO$^+$ APCs) made by the methods of the invention.

Preferably, the isolated IDO$^+$ APCs comprise at least 90% of the APC population expressing IDO at levels of at least 2-fold over background. More preferably, the isolated IDO$^+$ APCs comprise at least 95% of the APC population expressing IDO at levels of at least 2-fold over background. Also preferably, the isolated IDO$^+$ APCs comprise suppressor activity comprising an at least a 2-fold increase in T cell proliferation in the presence of an IDO inhibitor as compared to in the absence of an IDO inhibitor. In an embodiment, the isolated IDO$^+$ APCs express at least one antigenic polypeptide.

In an embodiment, the isolated cells comprise at least one cell surface marker that identifies the cells as expressing levels of indoleamine 2,3-dioxygenase (IDO) enzyme activity sufficient to suppress T cell proliferation (IDO$^+$ APCs). Preferably, the marker comprises CD123, CD11c and CCR6.

In an embodiment, the composition of the present invention includes a pharmaceutically acceptable carrier. Also preferably, the composition of the present invention includes one or more immunosuppressive pharmaceuticals in a unit dosage form.

In another aspect, the present invention comprises the generation of immunostimulatory cells. Such cells may be used to stimulate the immune response, as for example, to cancer-related antigens or viral-related antigens. Thus, in this aspect, the present invention comprises a method of making antigen-presenting cells (APCs) for enhancing T cell dependent immunologic activation in a subject comprising the steps of:

(a) isolating antigen-presenting cells (APCs) or their precursors (APC progenitors) from a subject; and (b) treating the isolated cells to select for APCs expressing levels of indoleamine 2,3-dioxygenase (IDO) enzyme activity not sufficient to cause suppression of T cell proliferation (IDO$^{LO}$ APCs).

Preferably, the IDO$^{LO}$ APCs comprise a population of APCs having less than 10% of the population expressing IDO at a level of greater than 2-fold over background. More preferably, the IDO$^{LO}$ APCs comprise a population of APCs having less than 5% of the population expressing IDO at a level of greater than 2-fold over background. Alternatively, the IDO$^{LO}$ APCs may be quantitated using a T cell proliferation assay such as a mixed leukocyte reaction or similar methods, wherein IDO$^{LO}$ APCs comprise an absence of suppressor activity comprising a less than a 1.5-fold increase in T cell proliferation in the presence of an IDO inhibitor as compared to in the absence of an IDO inhibitor. Preferably, the IDO inhibitor comprises 1-methyl-(D,L)-tryptophan, β-(3-benzofuranyl)-(D,L)-alanine, β-(3-benzo(b)thienyl)-(D,L)-alanine, or 6-nitro-(D,L)-tryptophan. Also preferably, the IDO inhibitor comprises 1-methyl-(D)-tryptophan or 6-nitro-(D)-tryptophan.

Preferably, the isolated APCs or APC progenitors comprise mature blood-derived dendritic cells, mature tissue dendritic cells, monocyte-derived macrophages, non-dendritic APCs, B cells, plasma cells, or any mixture thereof. Also preferably, the isolated APCs or APC progenitors comprise a cell type bearing markers of antigen presentation and costimulatory function. Also preferably, the APCs or APC progenitors are isolated from peripheral blood, bone marrow, lymph nodes or a solid organ from a human or other mammal.

The treatment to select for IDO$^{LO}$ APCs may comprise predetermined culture conditions or physical selection. In an embodiment, treatment of APCs and progenitor APCs to select for IDO$^{LO}$ APCs comprises culturing the cells in the presence of serum-free medium. In other embodiments, treatment of APCs and progenitor APCs to select for IDO$^{LO}$ APCs comprises culturing the cells in the presence of MCSF, or GMCSF, or interferon-α, or combinations thereof. In an embodiment, treatment of APCs and progenitor APCs to select for IDO$^{LO}$ APCs comprises culturing the cells with an agent to cause maturation of those APCs that express low levels of IDO (IDO$^{LO}$ APCs). Preferably, the maturation agents comprise TNFα, CD40-ligand (CD40L), activating anti-CD40 antibodies, cells engineered to express cell-surface CD40-ligand, proinflammatory bacterial or pathogen products, or any combination thereof. Alternatively (or additionally), the APCs may genetically engineered to express CD40-ligand. The treatment may also comprise culturing the cells in the presence of neutralizing antibodies for IL10 and/or TGFβ. Thus, for selection of IDO$^{LO}$ APCs, these agents may be combined singly, or added together with other agents used for the maturation of DCs (Jonuleit, H., et al., *Eur. J. Immunol.* 27: 315-3142 (1997); Reddy, A., et al., *Blood* 90: 3640-3646 (1997).

Alternatively, step (b) may comprise genetically modifying the APCs or APC progenitors such that the final preparation comprises APCs expressing levels of indoleamine 2,3-dioxygenase (IDO) enzyme activity not sufficient to suppress T cell proliferation (IDO$^{LO}$ APCs).

In an embodiment, the method utilizes cell surface proteins or other markers for selection of IDO$^{LO}$ cells from other APCs. Thus, in an embodiment, the method includes measuring expression of at least one cell surface marker that identifies the APCs as expressing levels of IDO not sufficient to suppress T cell proliferation ($IDO^{LO}$) or as expressing levels of IDO ($IDO^+$). Preferably, the cell surface marker is used to separate APCs that express low levels of IDO ($IDO^{LO}$ APCs) from APCs that express high levels of IDO sufficient to suppress T cell proliferation ($IDO^+$ APCs). The markers used for differential selection of $IDO^{LO}$ cells from $IDO^+$ cells include, but are not limited to, CD123, CD11c, CCR6, CD14 or any combination thereof. Alternatively, the method may include differential adhesion to a substrate to separate APCs that express levels of IDO not sufficient to suppress T cell proliferation ($IDO^{LO}$ APCs) from APCs that express levels of IDO sufficient to suppress T cell proliferation ($IDO^+$ APCs).

One object of the present invention is to develop immunogenic APCs that present a specific subset of antigens of interest. For example, APCs depleted of tolerance-inducing cells (i.e. $IDO^{LO}$ APCs) may be used to present antigens expressed by a tumor or a pathogen to a subject to increase the immune response to such antigens. Thus, in an embodiment the method includes exposing the treated APC preparation to at least one source of antigen after isolation and selection of $IDO^{LO}$ APCs. In an embodiment, the antigen comprises a at least one synthetic or natural polypeptide. Preferably, the antigen is expressed by a tumor. Also preferably, the antigen is expressed by a pathogen. Alternatively, the method may comprise transfecting or genetically engineering the $IDO^{LO}$ APCs to express at least one antigenic polypeptide.

In another aspect, the present invention comprises a method for increasing the number of non-suppressive antigen-presenting cells (APCs) in a subject comprising treating the subject to increase the population of APCs or their precursors (APC progenitors) expressing levels of indoleamine 2,3-dioxygenase (IDO) enzyme activity not sufficient to cause suppression of T cell proliferation ($IDO^{LO}$ APCs).

In another aspect, the present invention comprises a method for increasing the protective immune response in a subject comprising the steps of:

(a) isolating antigen-presenting cells (APCs) or their precursors (APC progenitors) from a first subject;

(b) treating the isolated cells to select for APCs expressing levels of indoleamine 2,3-dioxygenase (IDO) enzyme activity not sufficient to cause suppression of T cell proliferation ($IDO^{LO}$ APCs); and (c) administering the treated cells of step (b) back into the subject in an amount effective to generate a protective immune response in the subject.

Preferably, a protective immune response comprises a reduction in proliferation of tumor cells or a reduction in the clinical progression of a malignancy. Also preferably, a protective response is associated with a reduced pathogen load or increased resistance to at least one pathogen.

In an embodiment, the method is used to increase the immune response to a specific subset of antigens. Thus, in an embodiment, the method includes exposing the treated cells of step (b) to at least one source of antigen after isolation from the first subject. In an embodiment, the antigen comprises an natural or synthetic polypeptide. Preferably, the antigen is expressed by a tumor. Also preferably, the antigen is expressed by a pathogen. In another embodiment, the method comprises transfecting or genetically engineering the treated cells of step (b) to express at least one antigenic polypeptide.

The present invention also provides composition for increasing T cell activation. Such compositions may be used to increase the T cell response to antigens in a subject. In this aspect, the present invention comprises isolated antigen-presenting cells (APCs) selected as comprising APCs expressing levels of indoleamine 2,3-dioxygenase (IDO) enzyme activity not sufficient to cause suppression of T cell proliferation ($IDO^{LO}$ APCs). In another aspect, present invention comprises an isolated antigen-presenting cell (APC) selected as comprising levels of indoleamine 2,3-dioxygenase (IDO) enzyme activity not sufficient to cause suppression of T cell proliferation. In yet another aspect, the present invention comprises antigen-presenting cells (APC) comprising levels of indoleamine 2,3-dioxygenase (IDO) enzyme activity not sufficient to cause suppression of T cell proliferation ($IDO^{LO}$ APCs) made by the methods of the invention.

Preferably, the $IDO^{LO}$ cells comprise a population of APCs having less than 10% of the population expressing IDO at a level of greater than 2-fold over background. More preferably, the $IDO^{LO}$ cells comprise a population of APCs having less than 5% of the population expressing IDO at a level of greater than 2-fold over background. Also preferably, the $IDO^{LO}$ APCs comprise an absence of suppressor activity comprising less than a 1.5-fold increase in T cell proliferation in the presence of an IDO inhibitor as compared to in the absence of an IDO inhibitor.

In an embodiment, the $IDO^{LO}$ APCs comprise at least one cell surface marker that identifies the cells as expressing levels of indoleamine 2,3-dioxygenase (IDO) enzyme activity not sufficient to cause suppression of T cell proliferation ($IDO^{LO}$). Preferably, the marker comprises CD14. Also preferably, the marker causes preferential adhesion of the cells to plastic. Preferably, the composition comprises a pharmaceutically acceptable carrier.

APCs as $IDO^+$ and $IDO^{LO}$ Populations

The present invention relies on the discovery that APCs expressing high levels of the intracellular enzyme indoleamine 2,3-dioxygenase (IDO) are capable of suppressing T cell responses in vitro and in vivo. Thus, the present invention is based on the discovery that the tryptophan-degrading enzyme indoleamine 2,3-dioxygenase (IDO) is an intrinsic attribute of APCs that determines whether or not the APC is immunosuppressive or immunostimulatory.

Immunologic tolerance is operationally defined as the absence of an immunologic rejection response toward specific tissues or antigens. Conceptually, there are two types of tolerance: pre-existing tolerance to self, and acquired tolerance to new antigens. For example, imunocompetent mice become anergic (non-reactive) even to non-self antigens when these are introduced on tumors (Staveley-O'Carroll, K., et al., *Proc. Natl. Acad. Sci. USA*, 95: 1178-1183 (1998)). This anergy is apparently caused, not by the tumor cells themselves, but by cross-presentation of tumor antigens by tolerogenic bone marrow-derived APCs (Sotomayor, E. M., et al., *Blood*, 98: 1070-1077 (2001)).

Tolerogenic APCs are potent regulators of the immune response because they can create networks of immunoregulatory (suppressor) T cells. These regulatory T cell networks are apparently involved in both maintaining normal tolerance to self, and also in mediating a state of acquired unresponsiveness to non-self antigens (e.g. Sakaguchi, S., *Cell,* 101: 455-459 (2000); H. Waldmann and S. Cobbold, *Immunity,* 14: 399-406 (2001); Shevach, E. M., *J. Exp. Med.,* 193: F41-F46 (2001)). For example, it has been shown that tumor-specific regulatory T cells exist, and that blocking or depleting these cells facilitates the ability to break tolerance to tumor antigens (Sutmuller, R. P. M., et al., *J. Exp. Med.,* 194: 823-832 (2001); van Elsas, A., et al., *J. Exp. Med.,* 190: 355-366 (1999); van Elsas, A., et al., *J. Exp. Med.,* 194: 481-490 (2001)). Once established, this type of unresponsiveness is self-perpetuating, transferable, and can even "spread" to encompass new antigens encountered in the same context as those to which the network is already tolerant (S. Cobbold and H. Waldmann, *Curr. Opin. Immunol.*, 10: 518-524 (1998)). When present, regulatory T cells tend to be dominant, enforcing functional tolerance throughout the entire immune system even in the face of other, non-tolerant T cells (Honey, K., et al., *Immunol. Res.*, 20: 1-14 (1999)). It is known that certain types of human APCs are able to promote such regulatory T cells (Jonuleit, H., *Trends in Immunol.* 22: 394-400 (2001); Dhodapkar, M. V., et al., *J. Exp. Med*, 193: 233-238 (2001)). However the mechanism by which this occurs is unknown. Clearly, the ability to create such potent regulatory T cells is highly desirable in settings such as organ transplantation or autoimmunity. Conversely, it is undesirable (but often occurs) to inadvertently create such cells when immunizing against antigens (e.g. from pathogens or tumors).

The enzyme indoleamine 2,3-dioxygenase (IDO) is an intracellular heme-containing enzyme that catalyzes the initial rate-limiting step in tryptophan degradation along the kynurenine pathway (M. W. Taylor and G. Feng, *FASEB J.*, 5, 2516-2522 (1991)). It has been proposed that IDO suppresses T cell proliferation by degrading tryptophan in the local environment (Munn, D. H., et al., *J. Exp. Med.*, 189: 1363-1372 (1999)). Two types of human APCs, (1) monocyte-derived macrophages (Munn, D. H., et al., *J. Exp. Med.*, 189: 1363-1372 (1999)), and (2) monocyte-derived dendritic cells (Hwu, P., et al., *J. Immunol.* 164: 3596-3599 (2000)), which suppress T cell activation in vitro have been shown to express the tryptophan-degrading enzyme indoleamine 2,3-dioxygenase (IDO). In mice, IDO has been implicated in the tolerance displayed by the maternal immune system toward the immunologically disparate fetus (Mellor, A. L., et al., *Nat. Immunol.* 2: 64-68 (2001); Munn, D. H., et al., *Science*, 281: 1191-1193 (1998)), as well as in acquired tolerance toward antigens presented by murine CD8$\alpha^+$ dendritic cells (Grohmann, U. et al., *J. Immunol.*, 167: 708-714 (2001)). Also, IDO is required for the induction of spontaneous tolerance by liver allografts (Miki, T., et al., *Transplantation Proceedings* 33: 129-130 (2000)), a process which is thought to be mediated by graft associated DCs (Thompson, A. W. and Lu., L., *Immunol. Today* 20: 27-31 (1999)). A direct mechanistic link between IDO gene expression and suppression of antigen-specific T cell responses in vivo has been shown in a mouse model by the inventors (Mellor, A. L., et al., *J. Immunol.* 168: 3771-3776 (2002)), wherein transfection of the mouse IDO gene into murine cell lines causes: (1) suppression of T cell responses to antigens presented by the IDO-expressing cell lines; and (2) abrogation of the ability of the cells to prime an allogenic T cell response in vivo to antigens.

There are several ways to measure IDO expression. As defined herein, cells comprising high levels of IDO activity comprise: (1) a level of IDO activity sufficient to suppress T cell proliferation either in vitro or in vivo; (2) a level of IDO protein or RNA significantly above the background level of the assay; or (3) at least 90% of APCs in the preparation expressing IDO as enumerated on a cell-by-cell basis. For example, high level IDO expression (IDO$^+$) is defined by flow cytometry quantitatively on a cell by cell basis as expression of antigenic IDO protein at a level of at least 2-fold above background, more preferably, at a level of at least 5-fold above background, and even more preferably, at a level of at least 10-fold over background. In this assay, background may be defined as neutralization of an anti-IDO antibody using standard techniques such as binding with an excess of an immunizing peptide (polyclonal antibody assay) or binding of an isotype-matched control (monoclonal antibody assay).

Thus, in an embodiment of the present invention, tolerance-inducing IDO+ APCs comprise at least 90% of the APC population expressing IDO at levels of at least 2-fold over background, and more preferably, at least 95% of the APC population expressing IDO at levels of at least 2-fold over background.

IDO protein and RNA levels can also be measured by other techniques including western blot, immunohistochemistry, northern blot, reverse-transcriptase polymerase chain reaction (RT-PCR), or in situ hybridization. Preferably, using the techniques of immunohistochemistry or in situ hybridization, IDO expression is be measured on a cell-by-cell basis. Cells expressing IDO are defined relative to the appropriate negative control for the particular assay as understood by one skilled in the art. Preferably, the IDO-expressing APCs comprise at least 90% of the APC population in such an assay, and more preferably, at least 95% of the APC population. IDO can also be measured by western blot, northern blot, RT-PCR, and other assays that measure IDO in a bulk population. High level IDO expression (IDO$^+$) for a bulk population is defined as IDO-specific signal of at least 2-fold over the negative control for the particular assay; as understood by one skilled in the art, or preferably, at a level of at least 5-fold over background, and more preferably, at a level of at least 10-fold over background.

Low levels of IDO expression (IDO$^{LO}$) may also be defined by flow cytometry or other assays quantitatively on a cell-by-cell basis with reference to the percentage of cells expressing IDO. Thus, in an embodiment, IDO$^{LO}$ cells comprise APCs wherein a minority of APCs in the preparation expressing IDO protein at a level of at least 2-fold over background. In an IDO$^{LO}$ preparation of APCs, preferably less than 10% of the APCs express IDO protein at a level of at least 2-fold over background, more preferably less than 5% of the APCs express IDO protein at a level of at least 2-fold over background. Alternatively, IDO is measured by immunohistochemistry, in situ hybridization or other techniques that measure IDO on a cell-by-cell basis, and an IDO$^{LO}$ preparation is defined as comprising less than 20% IDO-expressing cells, or more preferably less than 10% IDO-expressing cells, and even more preferably, less than 5% IDO-expressing cells. Alternatively, IDO expression is measured in a bulk population, such that IDO-specific signal is less than 2-fold over the negative control for the particular assay.

Alternatively, an assay to measure biological activity such as a T cell proliferation assay is used to quantify IDO activity. A T cell proliferation assay includes, but is not limited to, a mixed leukocyte reaction (MLR) assay, or stimulation of T cells with antigen or mitogen.

Thus, in an embodiment, high level IDO expression (IDO$^+$) is defined as a greater than 2-fold increase in T-cell proliferation when an inhibitor of IDO is added to MLRs containing the preparation of interest. This assay provides a physiological basis to quantify the amount of T-cell proliferation that has been suppressed by IDO (i.e. the MLR without the IDO inhibitor compared to the MLR with the IDO inhibitor). Preferably, the MLR contains the APC preparation to be administered plus allogeneic or xenogeneic T cells. Alternatively, the T cell proliferation assay may contain the APC preparation to be administered plus autologous T cells and an antigen or mitogen to serve as the stimulus for T cell proliferation. High level IDO expression (IDO$^+$) is defined as a greater than 2-fold increase in T cell proliferation when an inhibitor of IDO is added to co-cultures containing the preparation of interest.

T cell proliferation assays may also be used to quantify low IDO activity. Thus, in an embodiment, low IDO activity (IDO$^{LO}$) is defined by an allogenic MLR or autologous antigen or mitogen-stimulation assay as less than 1.5 fold increase in T cell proliferation when an inhibitor of IDO is added to co-cultures containing the APC preparation of interest.

As defined herein, an inhibitor of IDO is an agent capable of preventing tryptophan degradation and/or kynurenine production by IDO enzyme in a cell free system, or by cells expressing IDO. For example, the inhibitor of IDO is an agent capable of preventing tryptophan degradation and/or kynurenine production by isolated human monocyte-derived macrophages activated by interferon-γ (Munn, D. H., et al., *J. Exp. Med.*, 189: 1363-1372 (1999)). Preferably, the inhibitor of IDO is an analogue of tryptophan. More preferably, the inhibitor of IDO is the (D) isomer analogue of tryptophan rather than the (L) analogue, as in some cases only the (D) isomer reveals true suppression of T-cell activation by IDO. Thus in an embodiment, the inhibitor of IDO comprises 1-methyl-(D,L)-tryptophan, β-(3-benzofuranyl)-DL-alanine (the oxygen analog of tryptophan) (1-MT), β-[3-benzo(b)thienyl]-(D,L)-alanine (the sulfur analog of tryptophan) (S. G. Cady and M. Sono, *Arch. Biochem. Biophys.* 291, 326 (1991)), or 6-nitro-(D,L)-tryptophan. More preferably, the inhibitor of IDO comprises 1-methyl-(D)-tryptophan or 6-nitro-(D)-tryptophan.

Thus, the present invention describes a method of making antigen-presenting cells (APCs) for enhancing T-cell tolerance comprising the steps of:

(a) isolating antigen-presenting cells (APCs) or their precursors (APC progenitors) from a first subject; and (b) treating the isolated cells to select for APCs expressing levels of indoleamine 2,3-dioxygenase (IDO) enzyme activity sufficient to suppress proliferation of T cells (IDO$^+$ APCs).

The present invention also describes a method of making antigen-presenting cells (APCs) for enhancing T-cell activation in an individual comprising the steps of:

(a) isolating antigen-presenting cells (APCs) or their precursors (APC progenitors) from a subject; and (b) treating the isolated cells to select for APCs expressing levels of indoleamine 2,3-dioxygenase (IDO) enzyme activity not sufficient to cause suppression of T cell proliferation (IDO$^{LO}$ APCs).

As defined herein, isolated APCs or progenitor APCs comprise populations of cells which are either able to express high levels of IDO (IDO$^+$ APCs) or which constitutively express low levels of IDO (IDO$^{LO}$ APCs) as measured by protein levels (flow cytometry), mRNA levels, or T cell proliferation assays. The isolated APCs or APC progenitors may comprise mature blood-derived dendritic cells, mature tissue dendritic cells, monocyte-derived macrophages, non-dendritic APCs, B cells, plasma cells, or any mixture thereof. In an embodiment, the isolated APCs or APC progenitors comprise a cell type bearing markers of antigen presentation and costimulatory function.

As defined herein, non-dendritic APCs comprise cells isolated directly from peripheral blood, bone marrow, or solid organ or tissue, or derived by in vitro culture of cells from peripheral blood, bone marrow, or solid organ or tissue, which cells do not express CD83, but which do express high levels of MHC class II antigen as well as at least one marker of APC function. Such markers of APC function include, but are not limited to, CD80, CD86, and B7-H1 (Dong et al., *Nature Med.*, 5: 1365-1369 (1999)). Such non-dendritic APCs may express high constitutive or inducible levels of IDO (IDO$^+$), low levels of IDO (IDO$^{LO}$), or may comprise a mixture of IDO$^+$ and IDO$^{LO}$ cells. Non-dendritic APCs include, but are not limited to, endothelial cells, tissue macrophages, and other cells expressing constitutive or inducible MHC II.

Non-dendritic APC include cultured blood-derived non-dendritic APCs. As defined herein, cultured blood-derived non-dendritic APCs comprise isolated peripheral blood mononuclear cells or a fraction thereof which following culture in vitro, do not express CD83 but do express high levels of MHC class II antigens as well as one or more markers of APC co-stimulatory function, such as, but not limited to, CD80, CD86 or B7-H1 (Dong et al., *Nature Med.*, 5: 1365-1369 (1999)), either constitutively or following exposure to maturation agents. Blood-derived non-dendritic APCs may be cultured in a medium with or without cytokines including, but not limited to, MCSF, GMCSF, IL4, IL3, IL 10, and TNFα. For example, in an embodiment, monocyte derived macrophages cultured in MCSF express high levels of IDO (IDO$^+$) (Munn, D. H., et al., *J. Exp. Med.*, 189: 1363-1372 (1999)). In another embodiment, CD14+/CD83– cells following culture in GMCSF+IL4 (which differentially adhere to plastic culture dishes) show no IDO mediated suppression (IDO$^{LO}$).

As defined herein, dendritic cells (DCs) comprise cells isolated directly from peripheral blood, bone marrow, organs or tissues, or derived by culture of cells isolated form peripheral, bone marrow, organs, tissues, or isolated CD34$^+$ stem cells collected from peripheral blood or bone marrow which cells express CD83 constitutively or following culture and maturation. DCs may be cultured in medium with or without cytokines, including, but not limited to GMCSF, IL4, IL3, and IL10.

Thus, as defined herein, immature dendritic cells (DCs) comprise DCs which express low levels of MHC class II antigens. As defined herein, low levels of MHC class II antigens are levels less than 2-fold greater than the negative control used in the assay to measure MHC class II antigen expression. Low levels of MHC class II may also be determined by comparison to mature DCs, and preferably comprise less than half the level of expression of MHC class II antigens found on mature DCs. MHC class II antigens may be measured by flow cytometry or other methods known in the art.

As defined herein, mature dendritic cells (DCs) comprise DCs which constitutively express high levels of MHC class II, or which have been treated with agents to cause maturation. As defined herein, high levels of MHC class II antigens are levels at least 2-fold greater than the negative control used in the assay to measure MHC class II antigen expression. Maturation can also be defined by comparison with the same population of DCs prior to treatment with agents to induce maturation. Defined in this way, maturation comprises at least a 2-fold upregulation of MHC class II antigen. Agents causing maturation comprise TNFα, CD40-ligand (CD40L), activating anti-CD40 antibodies, cells engineered to express cell surface CD40-ligand, or bacterial or pathogen products.

As defined herein, B cells comprise cells isolated from blood, bone marrow, lymph nodes or other tissue which express one or more markers of B cell differentiation such as, but not limited to, CD19, CD20, CD21, or surface immunoglobulin, wherein B cell markers may be measured by flow cytometry or other methods known in the art.

As defined herein, plasma cells comprise cells isolated from blood, lymph node or other tissue which express CD38 and cytoplasmic immunoglobulin as measured by flow cytometry or other methods known in the art.

As defined herein, selection of APCs which comprise IDO$^+$ APCs or IDO$^{LO}$ APCs may comprise selective culturing of the cells, including a predetermined regimen of cytokines and/or maturation agents. For example, a cytokine cocktail such as those known in the art (Jonuleit, H., et al., *Eur. J. Immunol.*, 27: 3135-3142 (1997)) may be employed. Thus, for selection of IDO$^+$ APCs or IDO$^{LO}$ APCs, cytokines may be combined singly, or added together with other agents used for the maturation of DCs (Jonuleit, H., et al., *Eur. J. Immunol.* 27: 315-3142 (1997); Reddy, A., et al., *Blood* 90: 3640-3646 (1997)). Selection also comprises physical selection techniques such as selecting immnunosorting of either IDO$^+$ or IDO$^{LO}$ cells. This is possible in that certain cell-surface antigens are associated with the IDO$^+$ and IDO$^{LO}$ phenotypes in APCs. In another embodiment, sorting comprises differential adherence of either IDO$^{LO}$ or IDO$^+$ cells to a substrate, presumably due to the expression of a specific cell surface marker that increases adherence.

T cell responses comprise allogeneic, xenogeneic, mitogen-driven, or antigen-driven responses. As defined herein, allogeneic T cells comprise T cells from a different individual of the same species, wherein such T cells proliferate in response to the presence of antigenic differences between the individuals. Xenogeneic T cells comprise T cells from an individual of a different species, wherein such T cells proliferate in response to the presence of antigenic differences between the species. As an example, T cells from a human recipient are xenogeneic to a porcine tissue donor.

As defined herein, CD40-ligand (CD40L) comprises isolated polypeptides, multimers of such peptides, or other compositions that bind to the extracellular binding region of a CD40 receptor of human, porcine or other origin (e.g. U.S. Pat. No. 6,290,972, incorporated by reference in its entirety herein).

As defined herein, proinflammatory bacterial and pathogen products comprise materials isolated from bacteria or other pathogens, or synthetic compositions derived from compounds produced by such organisms, including, but not limited to, lipopolysaccharide, CpG DNA, or monophosphoryl lipid A, which have as their defining property that they cause up-regulation of MHC class II molecules and/or costimulatory molecules (CD80 or CD86) on immature dendritic cells or non-dendritic APCs.

Thus, the present invention relies on the discovery that APCs may express high levels of IDO (IDO$^{+/POS}$) or low levels of IDO (IDO$^{LO/NEG}$) depending upon their hematopoietic lineage or state of maturation including the effect of conditioning and/or licensing signals encountered during development. As an example, FIG. 1 summarizes a proposed 3-step model for the regulation of IDO in the specific case of monocyte-derived dendritic cell DC differentiation. In step 1, monocytes begin to differentiate along the DC lineage. Step 2 occurs during later DC differentiation and maturation, when there is a cryptic commitment of each individual DC to subsequently become either IDO$^{+/POS}$ or IDO$^{LO/NEG}$. In an embodiment, those DCs that are negative for the cell surface marker CD123 commit to becoming IDO-negative (IDO$^{LO/NEG}$), suggesting that there is some degree of inherent heterogeneity or "pre-commitment" within in the circulating monocyte pool. In contrast, cells that are CD123 positive (CD123$^+$) still have the option to become either functionally IDO$^{+/POS}$ or IDO$^{LO/NEG}$, based on the conditions present during maturation. Thus, the CD123$^+$ cells will commit to the IDO$^{LO/NEG}$ (non-suppressor) phenotype if step 2 is driven solely by pro-inflammatory factors (e.g., CD40L, TNFα). If counter-regulatory cytokines such IL10 or TGFβ are present during maturation, then the CD123$^+$ cells will commit to the IDO$^{+/POS}$ (suppressor) phenotype.

Although the cells are committed at step 2, the functional IDO$^{+/POS}$ phenotype is not manifest until the DCs are activated, as for example, by the cytokine interferon-γ and possibly additional signals would come from the T cell during antigen presentation (step 3). Thus, although the same signal is delivered to both "non-suppressor" and "suppressor" DCs, the response of the DC to this signal, either IDO-mediated suppression of T-cell activation (IDO$^{+/POS}$), or downregulation of IDO (IDO$^{LO/NEG}$) such that the DC able to promote T-cell activation, depends on its history in step 2.

This model is consistent with existing models under which DCs undergo a "licensing" or "conditioning" process (corresponding to Step 2), either through direct cell-cell interaction with a helper T cell (Cella, M., et al., *J. Exp. Med.*, 184: 747-752 (1996); Ridge, J. P., et al., *Nature* 393: 474-478 (1998); Schoenberger, S. P., et al., *Nature* 393: 480-483 (1998); Bennett, S. R., et al, *Nature* 393: 478-480 (1998)) or via signals from the local cytokine milieu (Gallucci, S., et al., *Nat. Med.* 5: 1249-1255 (1999); Kourilsky, P,. et al., *Trends in Immunol.*, 22: 502-509 (2001)). One of the previously undescribed aspects of DC maturation shown by the model in FIG. 1 is that DCs can be "licensed" to suppress, and that ability of DCs to become suppressive may be regulated in vitro by culture conditions. Additionally, the model teaches that suppressive and non-suppressive DC populations can be distinguished by IDO expression (and cell surface markers associated with IDO$^{+/POS}$ and/or IDO$^{LO/NEG}$ phenotypes). In vivo, the cytokines driving commitment to the suppressor phenotype (e.g., IL10, TGFβ) may be provided by interaction with regulatory T cells (H. Waldmann and S. Cobbold, *Immunity* 14: 399-406 (2001); Maloy, K. G., et al., *Nature Immunol.*, 2: 816-822 (2001)) or may be present in a generalized tolerogenic milieu (Kourilsky, P. et al., *Trends in Immunol.*, 22: 502-509 (2001); Fiocchi, C., *J. Clin. Invest.*, 108: 523-526 (2001); Chen, W. et al., *Immunity* 22:14:715-725 (2001); Jonuleit, H. et al., *Trends in Immunol.* 22: 394-400 (2001)). In vitro, the regulatory cytokines may be supplied as recombinant cytokines during maturation.

Thus, the present invention teaches that this developmental scheme can be modeled in vitro to provide IDO$^+$ and IDO$^{LO}$ APCs. In humans, DC maturation has been associated with improved antigen-presenting function (Dhodapkar, M. V., et al., *J. Clin. Invest.* 105: R9-R14 (2000)) which as often been assumed to correspond to a loss of tolerogenic activity (Dhodapkar, M. V., et al., J. Exper. Med., 193: 233-238 (2001); Roncarolo, M. G. et al., J. Exp. Med. 193: F5-F9 (2001)). However, maturation may not be associated with a loss of tolerogenic activity. Instead, tolerance may be related to an additional signal, as yet undescribed, and which is distinct from other antigen presentation and co-stimulatory factors (Albert, M. L., et al., *Nature Immunol.*, 2: 1010 (2001); Shortman, K., et al., *Nature Immunol.*, 2: 988-989 (2001); T. Blankenstein and T. Shuler, *Trends Immunol.*, 23: 171-173 (2002)). The present invention teaches that this additional signal is the expression of IDO, such that mature DCs that express IDO will be tolerogenic and mature DCs that do not express IDO will be immunogenic.

Thus, the inventors believe that immature DCs are generally tolerogenic because in immature DCs, the activating population is ineffective, and therefore the tolerogenic population, although not optimized, is unopposed. The significant drawbacks to using immature DCs for therapy are that: (1) such cells constitute an uncharacterized mixture of cells, and in many applications even a minor contaminating admixture of the undesired type of APC (i.e. immunogenic instead of tolerogenic) may render the APC population unusable or even harmful for the desired application; (2) immature DCs are inherently unstable and may mature (thus, providing an undesired and potentially activating population of cells); and (3) immature DCs are inherently poor antigen-presenting cells due to their immature status, so the tolerogenic subset does not function as effectively as would a pure population of mature tolerogenic DCs.

The present invention therefore provides a method to produce relatively pure populations of suppressive and nonsuppressive APCs. Most DCs and other APC populations contain a mixture of suppressive and nonsuppressive populations. The present invention teaches that the conditions under which the APCs are derived can markedly affect the ratio of tolerogenic APCs as compared to immunogenic APCs. Previously, the existence of different tolerogenic and immunogenic subsets in humans could not be shown, nor was it possible to isolate specific tolerogenic (or immunogenic) subsets of APCs. Thus, the ability to use APCs for clinical applications was severely compromised as the presence of immunosuppressive APCs in a preparation of cells being used to enhance the T cell response (e.g. an anti-tumor vaccine) would result in antagonism of the desired effect. Similarly, the presence of immunogenic APCs in a preparation of cells being used to suppress the T cell response (e.g. transplant therapy) would be counter-productive.

Figure 2:
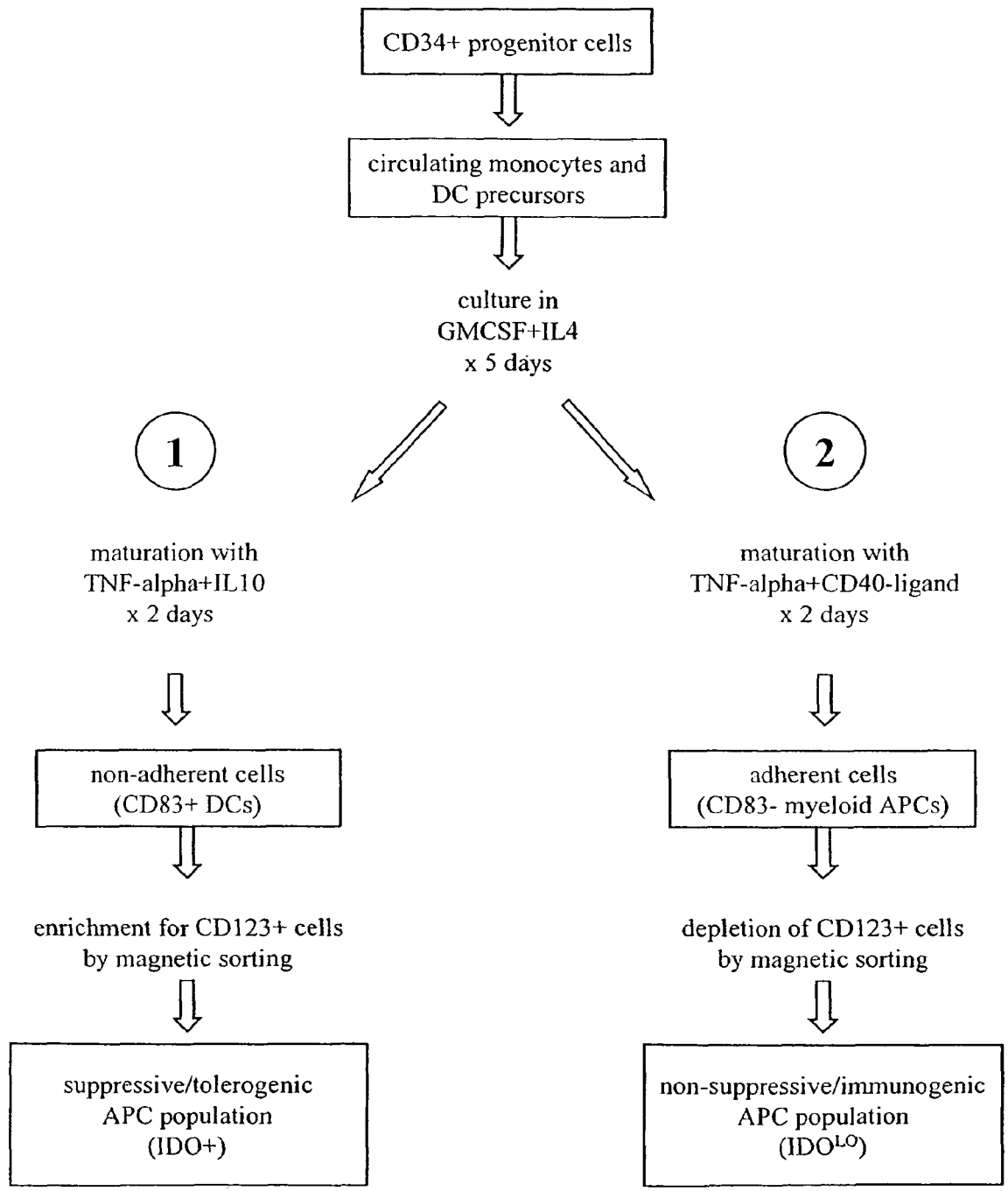
FIG. 2 shows a schematic representation of methods to generate subsets of peripheral blood-derived APCs which are either: (1) enriched in tolerance-inducing APCs, as for example, for use in transplant therapy; or (2) depleted of tolerance-inducing APCs, as for example, for use in anti-cancer vaccines, in accordance with an embodiment of the present invention.

Referring now to FIG. 2, APCs may be treated by culturing under conditions to favor production of (i.e. to select for) APCs that express high levels of IDO (IDO$^+$ APCs). In an embodiment, the isolated cells are cultured in medium which is essentially free of serum. Alternatively (or additionally), the cells may be cultured in the presence of macrophage colony stimulating factor (MCSF) or granulocyte-macrophage colony stimulating factor (GMCSF). When GMCSF is used, the concentration may range from 10 ng/ml to 1000 ng/ml, or more preferably from 50 ng/ml to 500 ng/ml. Alternatively (or additionally), the cells may be cultured in the presence of cytokines such as, but not limited to, TGFβ, IL10, IL 4, IL3, or any combinations thereof.

In an embodiment, the cells are also be treated with an agent to cause maturation of those APCs that express high levels of IDO. Preferably, the maturation agents comprise TNFα, IL10, TGFβ, CD40-ligand, activating anti-CD40 antibodies, cells engineered to express cell surface CD40-ligand, proinflammatory bacterial or pathogen products, or any combination thereof. Thus, these agents may be combined singly, or added together with other agents used for the maturation of DCs (Jonuleit, H., et al., *Eur. J. Immunol.*, 27: 3135-3142 (1997); Reddy, et al., *Blood* 90: 3640-3646 (1997)).

Following culture and maturation steps, further purification can be accomplished by differential adherence to a selected substrate chosen and optimized to yield preferential enrichment of the desired IDO$^+$ population, by methods described herein. Alternatively (or additionally), the purity of the IDO+ population is increased by immunosorting based on cell-surface antigens that associate with IDO$^+$ APCs. For example, in an embodiment, CD123 and CCR6 are associated with IDO$^+$ APCs and CD14 is associated with IDO$^{LO}$ APCs. Thus, the present invention contemplates that IDO$^+$ APCs isolated directly from tissues may only require maturation and immunosorting to comprise a pure population. Alternatively, when using CD34$^+$ APC progenitors, culture may be required for differentiation, and the cytokines chosen for use during culture are selected based on their ability to increase the IDO$^+$ population.

FIG. 2 also shows that APCs may be treated by culturing under conditions to favor production of APCs that express low levels of IDO (IDO$^{LO}$ APCs). For example, cells may be cultured in the presence of GMCSF+IL4 and then matured in the presence of TNF-α and CD40 ligand. In an embodiment, APCs are cultured in the presence of neutralizing antibodies to IL10 and TGFβ. The cells may also be treated with an agent to cause maturation of those APCs that express low levels of IDO. Preferably, the maturation agents comprise TNFα, CD40-ligand, activating anti-CD40 antibodies, cells engineered to express cell-surface CD40-ligand, proinflammatory bacterial or pathogen products, or any combination thereof. Thus, these agents may be combined singly, or added together with other agents used for the maturation of DCs (Jonuleit, H., et al., *Eur. J. Immunol.*, 27: 3135-3142 (1997); Reddy, et al., *Blood* 90: 3640-3646 (1997)).

As described above, and referring now to FIG. 3, the present invention further includes the step of measuring expression of at least one cell surface antigenic marker that identifies the cells as expressing high levels of IDO (IDO$^+$ APCs) or not expressing high levels of IDO (IDO$^{LO}$ APCs). Preferably, the absence or presence of the cell surface marker associated with high IDO is used to select for, and isolate, APCs that express high levels of IDO (IDO$^+$ APCs) from APCs that do not express high levels of IDO (IDO$^{LO}$ APCs). For example, markers associated with high levels of IDO in APCs comprise CD123 and CCR6. A less preferred marker is CD11c. In an embodiment, the presence of a cell-surface marker associated with low levels of IDO expression (IDOLO) is used to deplete the preparation of non-tolerogenic cells. Preferably, a marker associated with low levels of IDO in APCs is CD14. For example, in an embodiment, monocytes may be treated with a cytokine cocktail to induce differentiation and expression of IDO. The cells which express high levels of IDO, and are tolerance-inducing, are then separated from those cells which do not express IDO using at least one cell surface marker which shows a correspondence with IDO expression.

In another embodiment, the expression of uncharacterized cell surface proteins is used to facilitate separation of IDO$^+$ cells from IDO$^{LO}$ APCs. For example, in an embodiment, cells cultured in serum-free medium display enhanced adherence of the IDO$^{LO}$ APCs to the plastic culture dish. Thus, by selecting those cells which do not adhere to the plastic dish, a population of IDO$^+$ cells is selected.

Figure 4:
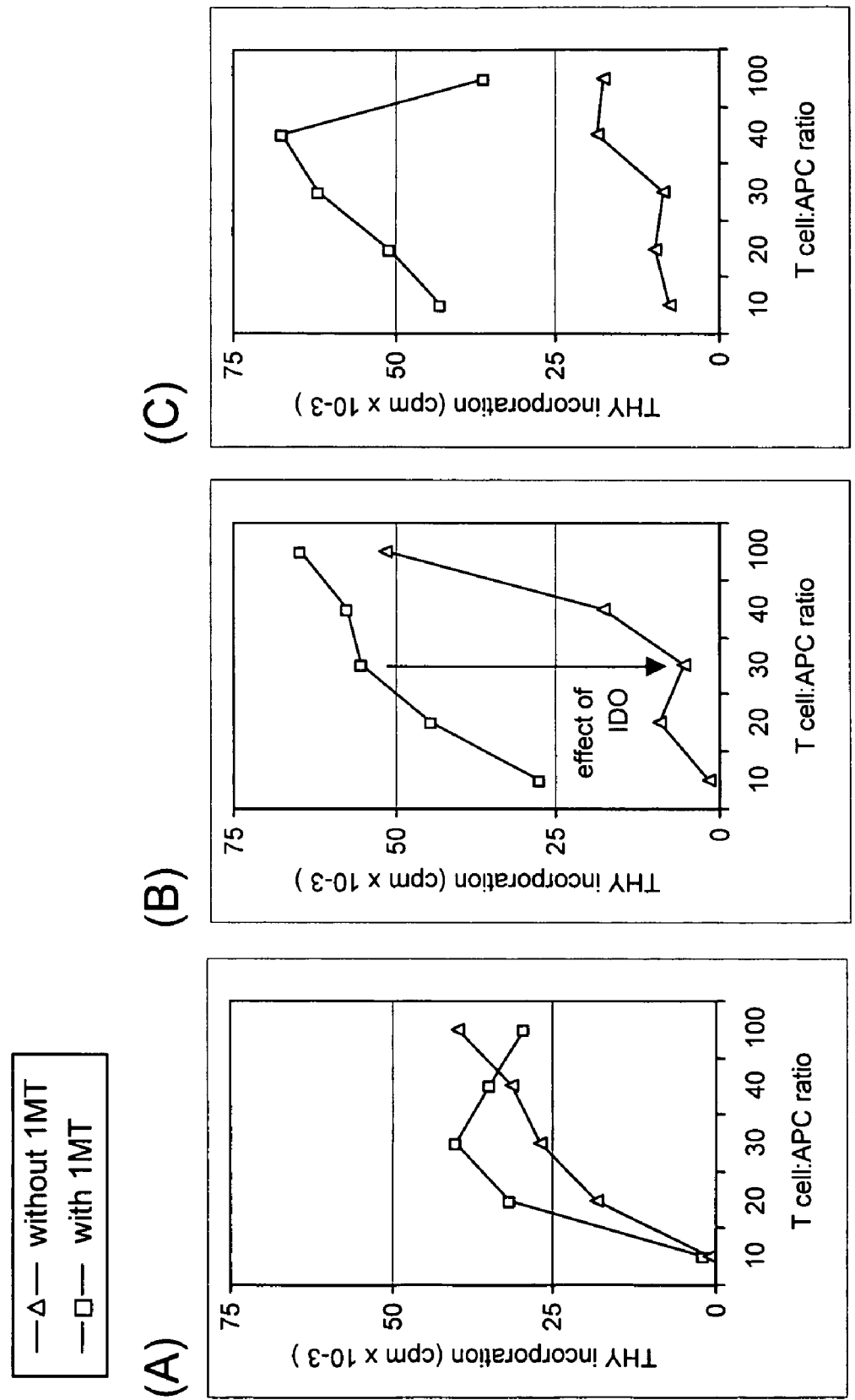
FIG. 4 shows the regulation of IDO during maturation in accordance with an embodiment of the present invention wherein (A) shows DCs cultured in GMCSF+IL4 for 7 days with and without the addition of 1-methyl-(D)-tryptophan; (B) shows the same DCs matured with a cocktail of cytokines (IL1β, TNFα, IL6, prostaglandin E2 (PGE2)); and (C) shows the same DCs matured with monocyte-conditioned medium. In all groups there is significant IDO-mediated suppression.

For example, and referring now to FIG. 4, DCs (immature) cultured in serum-free medium and enriched by non-adherence of IDO$^+$ cells to plastic culture wells (i.e. the IDO$^{LO}$ cells adhere) show moderate suppression of allogeneic T cell proliferation when still immature (FIG. 4A). Suppression may be measured as the finding more APCs (i.e. a low T cell:APC ratio) results in less T cell proliferation (FIG. 4A). Preferably, the inhibition is substantially due to IDO expression, as evidenced by reversal of the inhibition by 1-methyl-(D)-tryptophan (1-MT), an inhibitor of IDO. In contrast, mature DCs exhibit a much higher level of suppression, with suppression occurring even at T cell: APC ratios of 100:1 (FIGS. 4B and 4C). Addition of 1-MT (to inhibit IDO mediated suppression) causes a significant increase in T cell proliferation, to levels greater than immature DCs. Thus, contrary to current models, using the methods of the present invention, maturation actually enhances the suppression of T cells, and the enhanced suppression is due to IDO.

Figure 5:
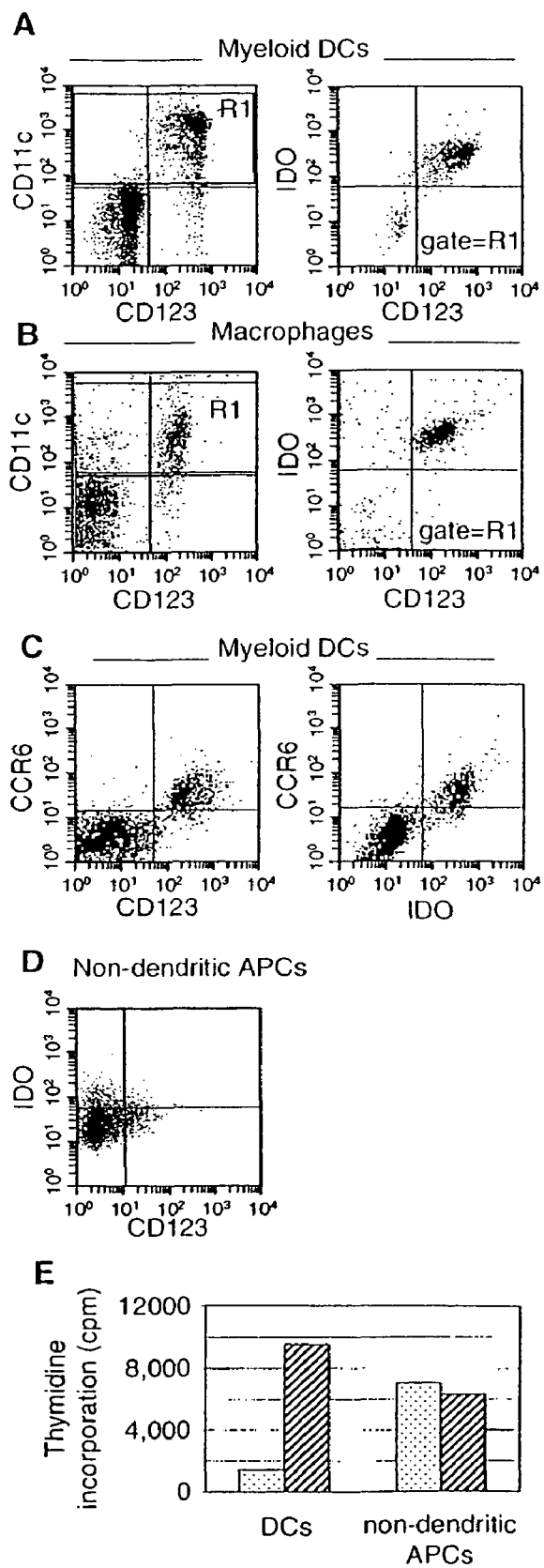
FIG. 5 shows expression of CD123, the chemokine receptor CCR6, and indoleamine 2,3-dioxygenase (IDO) by antigen-presenting cells in accordance with an embodiment of the present invention. In panels (A) and (B), human monocytes were cultured to produce myeloid dendritic cells (A) or macrophages (B), and then both groups received interferon-γ during the final 18 hrs of culture and harvested cells were triple-stained for CD123, CD11c and IDO. In (A) and (B), panels on the right show expression of IDO and CD123 in the gated CD11c⁺ population shown on the left. In (C) myeloid dendritic cells, cultured as in panel (A), were triple-stained for CD123, IDO, and the chemokine receptor CCR6. Both panels show the entire (ungated) population. In (D), the adherent (non-dendritic) population of APCs is shown, taken from a culture similar to panel (A) but using serum-free conditions. Cells were stained for IDO and CD123. Panel (E) compares IDO-mediated suppression by DCs and non-dendritic APCs from the same culture where IDO-mediated suppression is the difference in thymidine incorporation in T cells in the absence (stippled bars) vs. the presence (striped bars) of 1-methyl-(D,L)-tryptophan (1-MT).

Referring now to FIG. 5, cultured blood-derived APCs derived in bovine serum based medium (and not fractionated by differential adherence) produce a preparation comprising a mixture of IDO$^+$ and IDO$^{LO}$ cells. In an embodiment, a population of immature DCs which express the cell surface marker CD123 (CD123+) constitutively express immunoreactive IDO protein (FIGS. 5A and C for myeloid DCs derived in GMCSF+IL4; FIG. 5B for macrophages derived in MCSF, respectively). Maturation for 2 days with TNFα, or with CD40L, or with a published cocktail of cytokines (Jonuleit H., et al., *Eur. J. Immunol.*, 27: 3135-3142 (1997), or monocyte-condition medium (Reddy et al., *Blood* 90: 3640-3646 (1997)) does not affect IDO expression in the subset of CD123+ cells (not shown). In an embodiment, CD123 positive (CD123$^+$) cells expressing high levels of IDO (IDO$^+$) also express high levels of the cytokine receptor CCR6 (FIG. 5C). In contrast, cells selected as adhering to the culture dishes comprise primarily IDO$^{LO}$ non-dendritic APCs. Preferably, expression of IDO protein correlates with the ability of the cells to stimulate T cell proliferation as measured by tritiated thymidine incorporation into T cell DNA (FIG. 5E).

Association of Cell Surface Markers with IDO Expression

Figure 3:
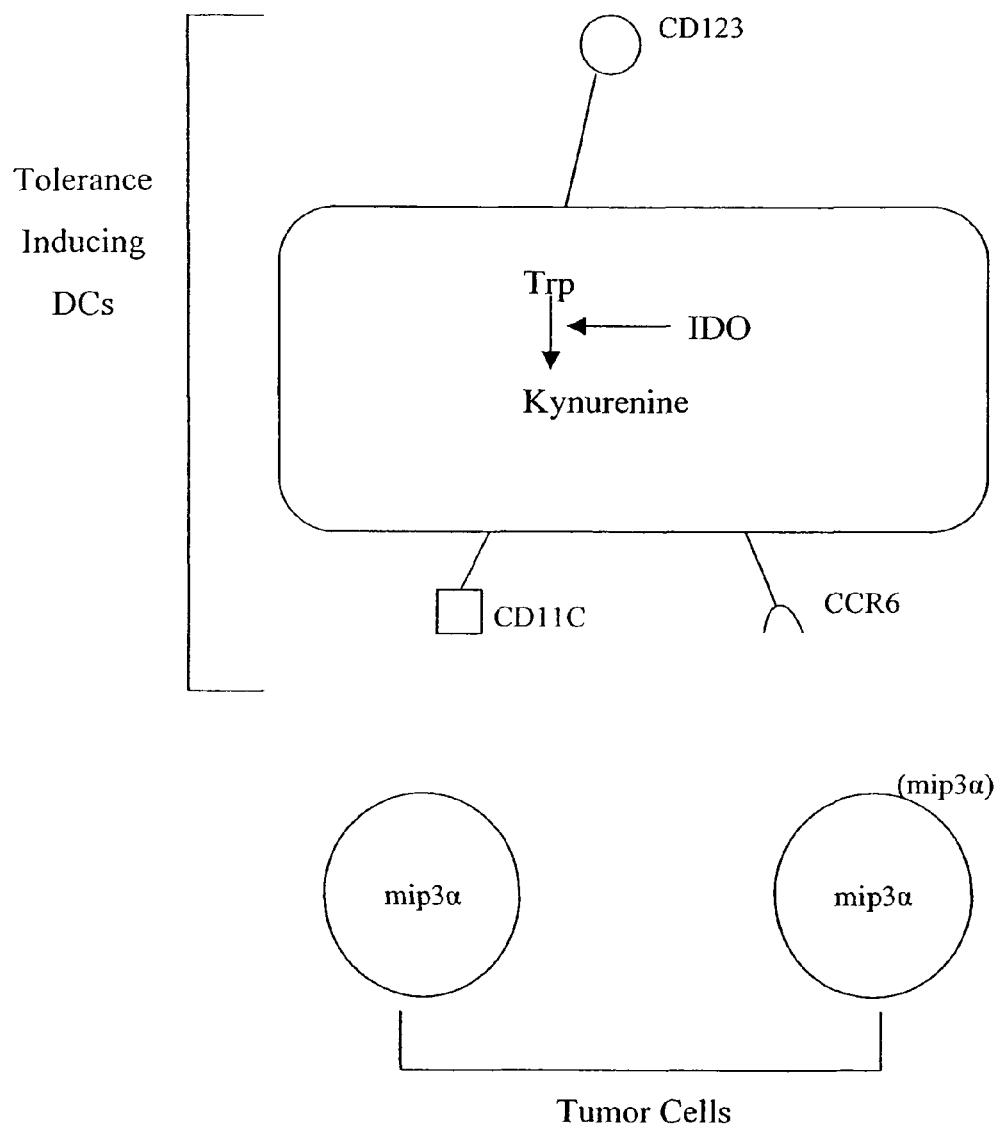
FIG. 3 shows a schematic representation of tolerance-inducing antigen-presenting cells (APCs) comprising expression of intracellular indoleamine 2,3-dioxygenase (IDO), cell surface markers CD123, CD11c, and the chemokine receptor CCR6 juxtaposed next to tumor cells that express mip-3α, in accordance with an embodiment of the present invention.

Because IDO is an intracellular enzyme, expression of the enzyme is not easy to detect in the intact (i.e. living) cell. Thus, the present invention utilizes the discovery that specific cell surface markers are associated with expression of IDO in antigen-presenting cells (FIG. 3).

For markers associated with cells having high levels of IDO expression (IDO$^+$), the marker preferably comprises is a cell surface protein (antigen) for which greater than 75% of the cells express high levels of IDO by flow cytometry or suppression of T cell proliferation as measured using T cell proliferation assays, and more preferably, for which greater than 90% of the cells express high levels of IDO by flow cytometry or suppression of T cell proliferation as measured using T cell proliferation assays, and even more preferably, for which greater than 95% of the cells express high levels of IDO by flow cytometry or suppression of T cell proliferation as measured using T cell proliferation assays.

In an embodiment, the cell surface marker associated with IDO expression is CD123. CD123 (the IL3-receptor α chain) is expressed on the small population of lymphoid-lineage "plasmacytoid" dendritic cells in peripheral blood (Liu, Y. J., *Cell*, 106: 259-262 (2001)), but it is also expressed at lower levels on a poorly-defined subset of myeloid-lineage dendritic cells in vivo (Olweus, J., et al., *Proc. Natl. Acad. Sci., USA*, 94: 12551-12556 (1997); Summers, K. L., et al., *Am. J. Pathol.*, 159: 285-295 (2001)).

Referring now to FIG. 5, preferably there is a 1:1 correspondence between APCs expressing IDO (IDO$^+$) and at least one cell surface marker. For example, in an embodiment, monocyte-derived DCs cultured for 7 days in GMCSF+IL4 (FIG. 5A) or macrophage-derived DCs cultured in MCSF (FIG. 5B) display a discrete subset of cells that express high levels of IDO (IDO$^+$), and express the cell surface marker CD123 (FIGS. 5A and B).

In addition, other cell surface markers may be used to identify IDO$^+$ cells. Thus, in an embodiment, a majority of IDO$^+$ APCs express the myeloid-lineage marker CD11c (FIGS. 5A and B).

Preferably, another marker highly associated with IDO expression is the chemokine receptor CCR6. CCR6 is the receptor for the chemokine mip-3α, a chemotactic factor for immature dendritic cells (Yang, D., et al., *J. Immunol.*, 163: 1737-1741 (1999)). Different subsets of dendritic cells express distinct patterns of chemokine receptors (Sozzani, S., et al., *J. Leukocyte Biol.* 66: 1-9 (1999)). CCR6 is expressed on CD34$^+$-derived dendritic cells at immature stages of differentiation, and on immature monocyte-derived dendritic cells cultured with transforming growth factor (TGF)-β, but is lost under some conditions when dendritic cells mature (Yang, D., et al., *J. Immunol.* 163: 1737-1741 (1999)). The present invention shows that under conditions favoring high expression of IDO, over 90% of APCs which express IDO also express CCR6 (FIG. 5C). Thus, IDO-expressing, tolerance-inducing APCs may comprise the cell surface markers CD123, CCR6, and in some cases, CD11c.

The specific pattern of markers that identifies the IDO$^+$ (or IDO$^{LO}$) population varies depending on the conditions used to isolate and culture the APCs. For example, CD11c is expressed at low levels in IDO$^{LO}$ cells cultured in bovine calf serum based medium (high seeding density and no differential adherence selection; FIG. 5A) but is expressed at higher levels for the IDO$^{LO}$ culture in serum-free medium (low seeding density and a final fractionation by differential adherence of non-dendritic APCs to the culture dish).

In an embodiment, enrichment using the cell surface marker alters the composition of the preparation such that it displays a higher level of IDO activity as measured by suppression of a T cell proliferation assay (e.g. an allogenic MLR). For example, and referring now to FIG. 6, CD123 enriched (CD123$^+$) APCs are markedly less efficient at stimulating T-cell proliferation than either the original unfractionated mixture, or the CD123 depleted subset (CD123$^{LO}$) that remains after sorting. The lack of T-cell activation is due to IDO expression, as shown by the ability of the IDO inhibitor, 1-methyl-(D,L)-tryptophan (1-MT), to prevent suppression. Thus, addition of 1-MT allowed the APCs to stimulate T-cell proliferation at near control levels, indicating that IDO is involved in the suppression. Enrichment may be accomplished by positive selection using magnetic beads comprising antibodies to the marker of interest, adhesion, flow cytometric sorting or other selections techniques known in the art.

Alternatively, when a pure population of IDO$^+$ APCs are desired, cell sorting techniques may be used to generate a population of APCs depleted of IDO$^{LO}$ cells using a cell surface antigen that correlates with low levels of IDO expression. Preferably, the cell surface antigen is a marker for which greater than 75% of the antigen-bearing cells do not express high levels of IDO by flow cytometry or suppression of T cell proliferation assays, more preferably, greater than 90% of the antigen-bearing cells do not express high levels of IDO by flow cytometry or suppression of T cell proliferation assays, and even more preferably, greater than 95% of the antigen-bearing cells do not express high levels of IDO by flow cytometry or suppression of T cell proliferation assays.

In an embodiment, the marker associated with IDO$^{LO}$ cells comprises CD14. CD14 (the endotoxin-binding protein receptor) is a well-accepted marker for cells of the monocyte-macrophage lineage (Szabolcs, P., et al., *Blood* 87: 4520-30 (1996)). Monocyte-derived dendritic cells down-regulate CD14 to undetectable (background) levels when they differentiate along the dendritic cell lineage (Pickl, W. F., et al., *J. Immunol.* 157: 3850-3859 (1996)). Mature myeloid dendritic cells do not express CD14 (K. Shortman and Y.-J. Liu, *Nature Reviews: Immunology* 2: 151-161 (2002)). Thus, in a culture comprising both mature DCs and a second population of non-dendritic APCs expressing CD14, the expression of CD14 can be used to distinguish between the two populations.

Thus, in yet an embodiment, a population of cells comprising low levels of IDO expression (IDO$^{LO}$) is generated by depleting the APCs of IDO$^+$ APCs (e.g. by selection with CD123 or other markers associated with high IDO) or by positive selection for markers associated with low IDO expression, such as CD14.

In yet another embodiment, the expression of uncharacterized cell surface proteins is used to facilitate separation of IDO$^+$ cells from IDO$^{LO}$ cells. For example, cells cultured in serum-free medium display enhanced adherence of the IDO$^{LO}$ APCs to the plastic culture dish. Thus, by selecting those cells which do not adhere to the plastic dish, a population of IDO$^+$ cells is selected. Examples of substrates which may be used for selection of cells by adherence include, but is not limited to, plastic (for example, plastic culture flasks or petri dishes), plastic treated by chemical or other means to facilitate adherence of tissue culture cells (tissue culture plastic), gas-permeable collection bags used in isolation and storage of blood products, filters, protein coatings, protein-lipid films and the like.

For example, FIG. 5D shows adherent cells taken from culture of monocytes in serum-free medium supplemented with GMCSF+IL4 and matured with a cocktail of TNFα, IL1β, IL6 and PGE2 as previously described (Jonuleit, H. et al., *Eur. J. Immunol.*, 27: 3135-3142 (1997)). In this type of culture, the adherent cells are normally discarded because they are not dendritic cells (Jonuleit, H., et al., *Eur. J. Immunol.*, 27: 3135-3142 (1997); Reddy, A., et al., *Blood* 90: 3640-3546(1997)). These cells are in fact quite valuable, as they represent a substantially purified preparation of $IDO^{LO}$ cells. These cells are not $IDO^+$, but they express markers of APC function (MHC class II, CD80, and CD86) at levels similar to non-adherent ($IDO^+$) cells from the same cultures. Greater than 95% of the $IDO^{LO}$ adherent cells express CD14, whereas less than 10% of the $IDO^{LO}$ adherent cells express CD 123 or CCR6.

$IDO^+$ APCs as Transplant Therapeutics

Cells which are tolerance-inducing APCs ($IDO^+$ APCs), may be used to promote tolerance in a subject. Thus, the invention comprises a method of preparing cells comprising tolerance-inducing APCs and the use of the cells to enhance immunological tolerance in an individual.

Figure 6:
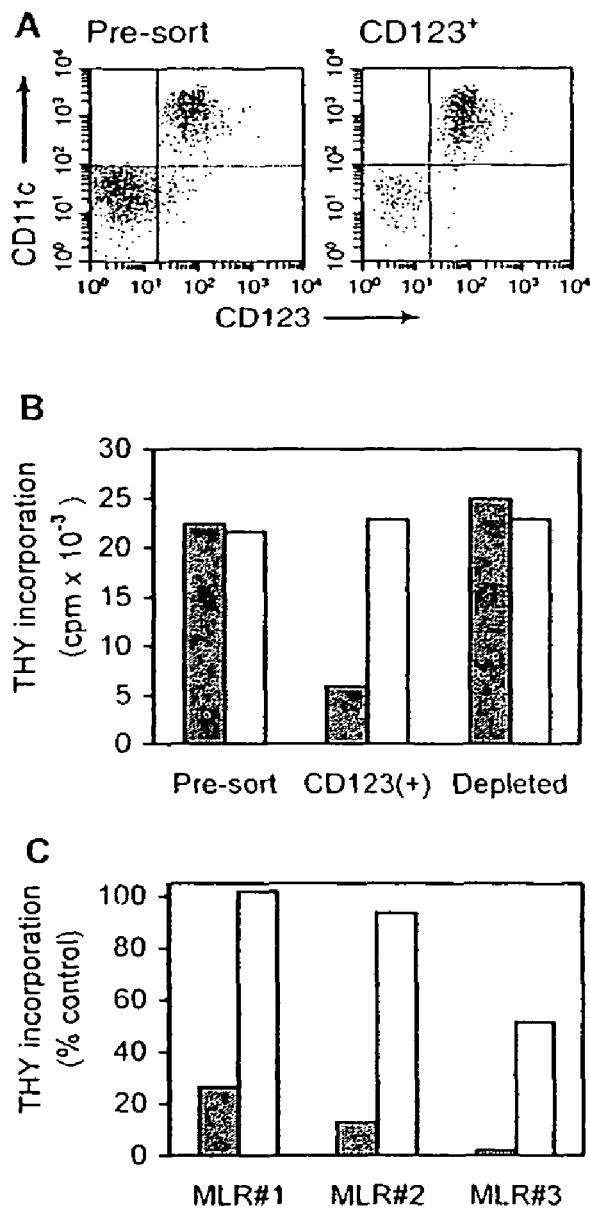
FIG. 6 shows suppression of allogeneic T cell proliferation by indoleamine 2,3-dioxygenase/CD123 expressing (IDO⁺/CD123⁺) dendritic cells in accordance with an embodiment of the present invention. Panel (A) shows myeloid dendritic cells which were activated for 24 hrs with TNFα, and labeled with anti-CD123 antibody and enriched by sorting (CD123$^+$) with goat anti-mouse secondary antibody conjugated to magnetic beads (immunosorting), wherein the left panel shows the population prior to enrichment and the right panel shows the population after enrichment. Panel (B) shows a comparison of the effect of CD123$^+$ enriched and CD123$^+$ depleted cells on allogeneic T cell proliferation as measured in a mixed-leukocyte reaction by thymidine incorporation in the absence (■) or the presence (□) of 1-methyl-(D,L)-tryptophan (1-MT; an inhibitor of IDO). Panel (C) shows experiments similar to panel (B), using 3 different pairs of donors, each allogeneic to the other, and each pair pre-tested to produce an active allogenic mixed leukocyte reaction (MLR) using sorted CD123$^+$ cells without (■) or with (□) 1-MT.

Thus, in one aspect, the present invention comprises a method to generate APCs for enhancing T cell tolerance towards cells, tissues and specific antigens in an individual comprising administration of a cell preparation in which the antigen-presenting cells (APCs) express high levels of IDO. In this aspect, the present invention relies on the discovery that APCs expressing high levels of IDO ($IDO^+$) are associated with reduced ability to activate T-cells (FIG. 6). In this way, $IDO^+$ APCs are used to increase the likelihood of acceptance of a graft or transplant from a first donor mammal to a second recipient mammal.

Thus, in one aspect, the present invention comprises a method for enhancing tolerance in a subject comprising the steps of:

(a) isolating antigen-presenting cells (APCs) or their precursors (APC progenitors) from a first subject;

(b) treating the cells to select for APCs that expressing levels of indoleamine 2,3-dioxygenase (IDO) enzyme activity sufficient to suppress proliferation of T cells ($IDO^+$APCs); and (c) administering the treated cells back to the original subject or to a second subject in an amount effective to generate a tolerance-promoting response in the recipient subject.

In an embodiment, a tolerance-promoting response reduces T-cell activation in the recipient subject. In an embodiment, the tolerance-promoting response prolongs the survival of transplanted cells or tissues in the recipient subject. In yet another embodiment, the treated cells are administered back to the original subject, and the tolerance-promoting response reduces the symptoms of an autoimmune disease in the subject.

As described herein, the present invention also comprises compositions for enhancing T cell tolerance. For example, such compositions may be used to promote acceptance of a tissue transplant or graft. Thus, the present invention also comprises a composition for enhancing T cell tolerance comprising antigen-presenting cells (APCs) selected as comprising APCs expressing levels of indoleamine 2,3-dioxygenase (IDO) enzyme activity sufficient to suppress proliferation of T cells ($IDO^+$ APCs). In one aspect, the compositions are be made by the methods of the present invention.

In an embodiment, $IDO^+$ APCs of the methods and compositions of the present invention are evaluated by measurement of the number of cells expressiong IDO. Preferably, the tolerance-inducing $IDO^+$ APCs comprise a cell population wherein at least 90% APCs expressing IDO at levels at least 2-fold greater than background, and more preferably at least 95% of the APCs express IDO at levels at least 2-fold greater than background, where background comprises a negative control for IDO.

Alternatively or additionally, IDO activity is quantified using a biological assay. In an embodiment, the tolerance-inducing $IDO^+$ APCs comprise suppression of T cell proliferation comprising at least a 2-fold increase in T cell proliferation in the presence of an IDO inhibitor as compared to T cell proliferation in the absence of an IDO inhibitor. Preferably, the inhibitors comprise 1-methyl-(D,L)-tryptophan, β-(3-benzofuranyl)-(D,L)-alanine, β-[3-benzo(b)thienyl]-(D,L)-alanine, or 6-nitro-(D,L)-tryptophan. More preferably, the inhibitors comprises 1-methyl-(D)-tryptophan or 6-nitro-(D)-tryptophan.

Preferably, the isolated APCs of the methods and compositions of the present invention comprise non-dendritic APCs, mature blood-derived dendritic cells, mature tissue dendritic cells, monocyte-derived macrophages, non-dendritic cells, B cells, plasma cells, or any mixture thereof. Also preferably, the APCs comprise markers of antigen presentation and co-stimulatory function. Preferably, the APCs are isolated from peripheral blood, bone marrow, lymph nodes or a solid organ from a mammal. More preferably, the subject is human.

One object of the present invention is to develop tolerance-promoting APCs that present a specific subset of antigens of interest. For example, tolerance-promoting APCs that present antigens from a donor may be administered to a transplant recipient to promote acceptance of a graft or transplant. Thus, in an embodiment, the subject from which the APCs or APC progenitors of the methods and compositions of the present invention are isolated comprises a tissue donor to a second subject. In another embodiment, the APCs or APC progenitors are isolated from a subject with an autoimmune disorder for subsequent preparation of $IDO^+$ APCs for use in treating the disorder.

Alternatively, the treated APCs of the methods and compositions of the present invention are exposed to at least one source of antigen after isolation from a first subject and selection as $IDO^+$ APCs. Preferably, the source of antigen comprises antigens expressed by a donor tissue graft. Also preferably, the source of antigen comprises protein or other material to which a patient has an autoimmune disorder (see e.g. Yoon, J.-W., et al., *Science* 284: 1183-1187 (1999) for examples of such proteins). Thus, in an embodiment, the subject from which the APCs or progenitor APCs are isolated comprises a patient with an autoimmune disorder. In an embodiment, the antigen comprises a purified, or a synthetic or recombinant polypeptide representing a specific antigen to which it is desired that tolerance be induced, or a short synthetic polypeptide fragment derived from the amino acid sequence of such an antigen. In an embodiment, the isolated APCs are transfected or genetically engineered to express at least one antigenic polypeptide (see e.g. Nair, S. K., et al., *Int. J. Cancer,* 82: 121-124 (1999); Heiser, A., et al., *J. Clin. Invest.*, 109: 409-417 (2002)).

In an embodiment, selection of $IDO^+$ cells of the methods and compositions of the present invention is facilitated using a cell surface marker that identifies the cells as expressing levels of IDO sufficient to suppress T cell proliferation ($IDO^+$ APCs) or expressing levels of IDO not sufficient to suppress T cell proliferation ($IDO^{LO}$ APCs) as described herein. The markers used may include, but are not limited to, CD123, CCR6, CD11c, CD14, or any combination thereof. Alternatively, the method may include differential adhesion to a substrate to separate APCs that express low levels of IDO ($IDO^{LO}$ APCs) from APCs that express high levels of IDO ($IDO^+$ APCs).

In an embodiment, the composition used to enhance T cell tolerance may include a pharmaceutically acceptable carrier. Alternatively, the composition may include one or more immunosuppressive pharmaceuticals in a unit dosage form.

As defined herein, a graft is a tissue specimen for transplantation from one mammal into another mammal. A host mammal is defined as the recipient of a graft specimen from a donor mammal, wherein the donor mammal and the host mammal are distinct entities. The grafts may either be homografts (a graft transplanted between mammals of the same species) or xenografts (a graft transplanted between mammals of the different species).

Isolation of mammalian cells for use as APCs of the present invention may be accomplished in accordance with the methods described in the Examples below. In addition, U.S. Pat. Nos. 5,849,589, 6,008,004, 6,194,204, and 6,274,378 describe isolation of mixed populations (i.e. not selected as tolerance-inducing) dendritic cells for use with the selection methods described herein and are hereby incorporated by reference in their entirety. Thus, U.S. Pat. No. 5,849,589 describes a method to induce differentiation of a monocyte into a dendritic cell (DC); U.S. Pat. No. 6,008,004 describes a DC precursor found among bone marrow $CD34^+$ cells; U.S. Pat. No. 6,194,204 describes a serial separation technique for isolating DC from peripheral blood; and U.S. Pat. No. 6,274,378 describes a method to increase the yield of DCs by culturing in GMCSF and IL-4. Those skilled in the art would be able to implement modifications to the disclosed methods of isolating cells for propagation as APCs without the exercise of undo experimentation.

U.S. Pat. Nos. 5,871,728 and 6,224,859, the disclosure of which is incorporated by reference in full herein, describe the isolation of dendritic cells from a donor for use in a transplant regimen. In contrast to the present invention, however, the dendritic cells in U.S. Pat. Nos. 5,871,728 and 6,224,859 B1 are cultured under conditions to remain in an immature state and therefore do not present DCs which are optimized to promote a tolerogenic response, nor are they purified to enrich for the tolerogenic population and/or the immunogenic population.

In an embodiment, autologous tolerogenic APCs are pulsed with an autoantigen (i.e. a protein or other material to which a patient has developed an autoimmune immunologic response as part of an autoimmune disorder) and administered back to a patient with an autoimmune disease. In another embodiment, tolerogenic APCs are isolated from the donor of a bone marrow transplant or hematopoietic stem-cell transplant and administered to a second subject who is receiving the transplant so as to prevent graft-versus-host disease in the recipient subject. Alternatively administration of tolerogenic APCs may be used to treat established graft-versus-host disease in a transplant recipient. In both cases, the goal is to initiate the development of a regulatory T cell response to a target antigen or set of antigens which will reduce the autoimmune or graft-versus-host T cell responses (H. Waldmann and S. Cobbold, *Immunity* 14: 399-406 (2001)).

Tolerogenic APCs may be administered prior to transplantation. In an embodiment, prophylactic administration may be commenced as early as 1 month prior to transplantation, and more preferably at about 1 week prior to transplantation. Alternatively, or additionally, administration may be at the time of transplantation and for several months following the transplantation, and at least several weeks following the transplantation, or even more preferably, several days following transplantation.

Immunosuppressive agents may also be included as part of the transplant regimen. Immunosuppressive reagents are typically administered at the time of transplantation and at least daily for some period afterwards. The amount of immunosuppressive agent is preferably adjusted based upon the success of the cell-driven response (i.e. the response as a result of administration of $IDO^+$ APCs.)

Pharmaceutical formulations can be prepared by procedures known in the art. For example, the compounds can be formulated with common excipients, diluents (such as phosphate buffered saline), tissue-culture medium, or carriers (such as autologous plasma or human serum albumin) and administered as a suspension.

The invention contemplates methods of administration which are well known in the art. Administration of the APCs of the present invention may include, but is not limited to, intravenous, subcutaneous, and intra-tumoral modes of administration. Additionally, the compounds are well suited to formulation as sustained release dosage forms of at least part of the preparation (e.g. immunosuppressive agents). Preferably, the cells are administered in a dose ranging from $5 \times 10^5$ to $5 \times 10^{10}$ cells per dose. More preferably, the cells are administered in a dose ranging from $5 \times 10^6$ to $5 \times 10^9$ cells per dose. Even more preferably, the cells are administered in a dose ranging from $5 \times 10^7$ to $1 \times 10^8$ cells per dose.

$IDO^{LO}$ APCs as Immunogenic Vaccines

The present invention also provides a means to isolate cells enriched for immunostimulatory APCs that show enhanced T-cell activation. For example, cells depleted of tolerance-inducing APCs can be used as anti-cancer vaccines or anti-viral vaccines to increase the host response to cancer or viral antigens, respectively.

In this aspect, the present invention comprises a method for increasing the protective immune response to at least one specified antigen in a subject comprising the steps of:

(a) isolating antigen-presenting cells (APCs) or their precursors (APC progenitors) from a subject;

(b) treating the cells to select for APCs expressing levels of indoleamine 2,3-dioxygenase (IDO) enzyme activity not sufficient to cause suppression of T cell proliferation ($IDO^{LO}$ APCs); and (c) administering the treated cells back to the subject in an amount effective to generate a protective immune response in said subject.

In an embodiment, a protective immune response comprises a reduction in size of a tumor or a reduction in the clinical progression of a malignancy. In another embodiment, a protective immune response is associated with increased resistance to at least one pathogen. For example, such increased resistance to a pathogen may comprise an increased resistance to infection, a reduced pathogen load, or increased production of pathogen specific antibodies or T cells.

The present invention also comprises compositions for increasing T cell activation. Such compositions are useful for generating a protective immune response. Thus, in another aspect the present invention comprises isolated antigen-presenting cells selected as comprising APCs expressing low levels of indoleamine 2,3-dioxygenase (IDO) enzyme activity ($IDO^{LO}$), wherein the $IDO^{LO}$ cells comprise a population of APCs expressing IDO at a level not sufficient to cause suppression of T cell proliferation ($IDO^{LO}$ APCs). The IDO$^{LO}$ APCs may be prepared by the methods described in the present invention or other methods known in the art.

Preferably, IDO$^{LO}$ cells of the methods and compositions of the present invention comprise a population of APCs having less than 10% of the population expressing IDO at a level of greater than 2-fold over background. More preferably, IDO$^{LO}$ cells of the methods and compositions of the present invention comprise a population of APCs having less than 5% of the population expressing IDO at a level of greater than 2-fold over background. Also preferably, IDO$^{LO}$ APCs comprise non-suppressor activity quantified by a mixed leukocyte reaction as less than 1.5 fold increase in T cell proliferation in the absence of an IDO inhibitor as compared to T cell proliferation in the presence of an IDO inhibitor. Preferably, the IDO inhibitors comprise 1-methyl-(D,L)-tryptophan, β-(3-benzofuranyl)-(D,L)-alanine, β-[3-benzo(b)thienyl]-(D,L)-alanine, or 6-nitro-(DL)-tryptophan. Also preferably, the IDO inhibitors comprise 1-methyl-(D)-tryptophan or 6-nitro-(D)-tryptophan.

Preferably, the isolated APCs or progenitor APCs comprise mature blood-derived dendritic cells, mature tissue dendritic cells, monocyte-derived macrophages, non-dendritic APCs, B cells, plasma cells, or any mixture thereof. Also preferably, the isolated APCs progenitor APCs comprise a cell type bearing markers of antigen presentation and costimulatory function. Also, in preferred embodiments, the APCs progenitor APCs are isolated from peripheral blood, bone marrow, lymph nodes or a solid organ from a human or other mammal.

In an embodiment the treated APCs of the methods and compositions of the present invention are exposed to at least one source of antigen after isolation from a subject and selection as IDO$^{LO}$ APCs. Preferably, the antigen is a polypeptide expressed by a tumor. Alternatively, the antigen may be expressed by a pathogen. Preferably, the antigen comprises an unpurified tumor or viral preparation. In another embodiment, the antigen is a synthetic or recombinant protein representing a known antigen to which it is desired to induce an immune response, or a short synthetic polypeptide derived from the amino acid sequence of such a protein. In another embodiment, the APCs selected as IDO$^{LO}$ are transfected or genetically engineered to express at least one such antigenic protein or polypeptide.

In an embodiment, selection of IDO$^{LO}$ cells of the methods and compositions of the present invention is facilitated using a cell surface marker that identifies the cells as expressing high levels of IDO (IDO$^+$ APCs) or not expressing high levels of IDO (IDO$^{LO}$ APCs) as described herein. The markers used may include, but are not limited to CD123, CD11c, CCR6, CD14, or any combination thereof. Alternatively, the method may include differential adhesion to a substrate to separate APCs that express low levels of IDO (IDO$^{LO}$ APCs) from APCs that express high levels of IDO (IDO$^+$ APCs).

As described herein, the APCs selected as IDO$^{LO}$ APCs of the methods and compositions of the present invention may be exposed to at least source of antigen after isolation from said first subject. Preferably, the antigen is a polypeptide expressed by a tumor. Alternatively, the antigen may be expressed by a pathogen. For example, U.S. Pat. Nos. 6,228,640, 6,210,662, 6,080,409, 5,994,126, 5,851,756, and 5,582,831 describe the manipulation of isolated dendritic cells to produce immunostimulatory vaccines specific to certain antigens. The disclosures of U.S. Pat. Nos. 6,228,640, 6,210,662, 6,080,409, 5,994,126, 5,851,756, and 5,582,831 are hereby incorporated in full by reference.

Alternatively, the isolated APCs are transfected or genetically engineered to express at least one antigenic polypeptide (see e.g. Nair, S. K., et al., *Int. J. Cancer*, 82: 121-124 (1999); Heiser, A., et al., *J. Clin. Invest.*, 109: 409-417 (2002)

Antigens may also be physically introduced into cells. For example, U.S. Pat. No. 6,228,640 B1 describes pulsing DCs with tumor RNA or expression products to prepare APCs comprising expression of specific antigens. Also, U.S. Pat. Nos. 6,210,662 and 6,080,409 describe methods and compositions generated by activating APCs by contact with a polypeptide complex constructed by joining together a dendritic cell-binding protein (GMCSF) and a polypeptide antigen. U.S. Pat. Nos. 5,994,126 and 5,851,756 describes a method for producing mature DCs pulsed with antigen, including particulates where the antigenic material is expressed on the surface of the cells as immunogens for vaccines. U.S. Pat. No. 5,582,831 describes forumulation of tumor vaccines by exposing tumor cells to a cross-linking agent to generate antigenic protein complexes.

In an embodiment, the isolated APCs of the methods and compositions of the present invention further comprise at least one cell surface antigenic marker that identifies the cells as expressing low levels of IDO (IDO$^{LO}$ APCs) or expressing high levels of IDO (IDO$^+$ APCs). The marker may include, but is not limited to CD123, CD11c, CCR6, or any combination thereof. Alternatively, the method may include differential adhesion to a substrate to separate APCs that express low levels of IDO (IDO$^{LO}$ APCs) from APCs that express high levels of IDO (IDO$^+$ APCs).

The compositions comprising IDO$^{LO}$ APCs may also include a pharmaceutically acceptable carrier, where pharmaceutically acceptable carriers include, but are not limited to the carriers described herein.

Methods and Kits to Measure the Amount of Immunosuppressive Cells in a Mixed Population of APCs The present invention also describes methods to quantitate the levels of immunosuppressive APCs in a population of APCs. For most applications it would be preferable, if not absolutely required, to determine the nature of the cell population being used. For example, when utilizing a preparation of cells for inducing tolerance in a host, a level of contaminating IDO$^{LO}$ cells of less than 10%, and more preferably less than 5%, is desired. Conversely, when utilizing a preparation of cells for increasing the immune response in a host, the level of contaminating IDO$^+$ cells should be determined.

Thus, in one aspect, the present invention comprises a method to determine the number of tolerance-inducing antigen-presenting cells (APCs) in a cell population comprising measuring the number of cells expressing levels of indoleamine 2,3-dioxygenase (IDO) enzyme sufficient to suppress proliferation of T cells (IDO$^+$ APCs) in the cell population. In an embodiment, IDO is quantified on a cell-by-cell basis. In an embodiment, IDO is quantified in a bulk population of APCs.

In another aspect, the present invention comprises a kit for determining the number of tolerance-inducing antigen-presenting cells (IDO$^+$ APCs) in a cell population comprising reagents to measure levels of indoleamine 2,3-dioxygenase (IDO) enzyme in the APCs, wherein the reagents are packaged in at least one individual container.

The immunosuppressive IDO$^+$ APCs may also be quantified using a biological assay. Thus, in another aspect, the present invention comprises a method to quantify the ability of a population of APCs to suppress T cell proliferation comprising measuring the ability of the cell population to increase in T cell proliferation in the presence of an IDO inhibitor as compared to in the absence of an IDO inhibitor. The present invention also comprises a kit for determining the ability of a population of APCs to suppress T cell proliferation comprising an IDO inhibitor packaged in at least one individual container. In an embodiment, the kit includes individual assay vessels which provide a pre-determined cell density. Preferably, the assay vessels comprise round-bottomed or V-shaped wells.

IDO$^+$ APCs and mip-3α as Markers of Tumors

Because tolerance-inducing APCs reduce the host's ability to reject foreign antigens which are present on tumor cells, the presence of tolerance-inducing APCs in a tumor is associated with a less favorable prognosis than in cases where tolerance-inducing APCs are not present. Thus, the present invention also describes assessing the relative risk of tumor progression by assaying tissue from a tumor or tumor draining lymph node for antigen-presenting cells of myeloid-lineage which have high levels of expression of the intracellular enzyme indoleamine 2,3-dioxygenase (IDO).

Thus, in another aspect, the present invention comprises a method for assessing the relative risk of tumor progression in a subject comprising the steps of:

(a) assaying a sample of tissue from a tumor or tumor draining lymph node from a subject for expression of the enzyme indoleamine 2,3-dioxygenase (IDO); and (b) correlating the risk of tumor progression to IDO expression in the tissue sample, wherein IDO expression is positively correlated with an increase in the risk of tumor progression.

In an embodiment, the method further includes identification of cell surface markers associated with high IDO expression. Preferably, the cell surface markers comprise CD123, CD11c or CCR6.

The present invention also comprises kits for assessing the relative risk of tumor progression in a subject. For example, in one aspect, the present invention comprises a kit for assessing the relative risk of tumor progression in a subject comprising reagents for detection of the enzyme indoleamine 2,3-dioxygenase (IDO) in a sample of tissue from a tumor or tumor draining lymph node from a subject, wherein the reagents are packaged in at least one individual container. Preferably, the kit further comprises reagents for detection of cell surface or immunohistochemical markers associated with high IDO expression by APCs. More preferably, the cell surface markers detected using the kit comprise CD123, CD11c or CCR6.

The present invention also relies on the discovery that tumor cells that recruit tolerance-inducing APCs to the tumor exhibit increased tolerance. CCR6, a marker highly associated with IDO expression (IDO$^+$), is a receptor for the chemokine mip-3α, a chemotactic factor for immature dendritic cells (D. Yang, O. M. Howard, Q. Chen, J. J. Oppenheim, *J. Immunol.* 163: 1737-1741 (1999)). Elevated mip-3α expression has been seen in certain tumors (Bell, D., et al., *J. Exp. Med.*, 190: 1417-1426 (1999)). Thus, tolerance-inducing APCs that express receptors for chemoattractant factors secreted by the tumors play a role in the development of tumor-induced tolerance.

Thus, in another aspect, the present invention also comprises a method for assessing the risk of tumor progression in a subject comprising the steps of:

(a) assaying a sample of tissue from a tumor or tumor draining lymph nodes from a subject for mip-3α expression; and (b) correlating the risk of tumor progression to mip-3α expression in the tissue sample, wherein mip-3α expression is positively correlated with an increase in the risk of tumor progression.

In another aspect, the present invention comprises a kit for assessing the relative risk of tumor progression in a subject comprising reagents for detection of relative levels of expression of mip-3α in a sample of tissue from a tumor or tumor draining lymph node from a subject, wherein the reagents are packaged in at least one individual container.

Figure 8:
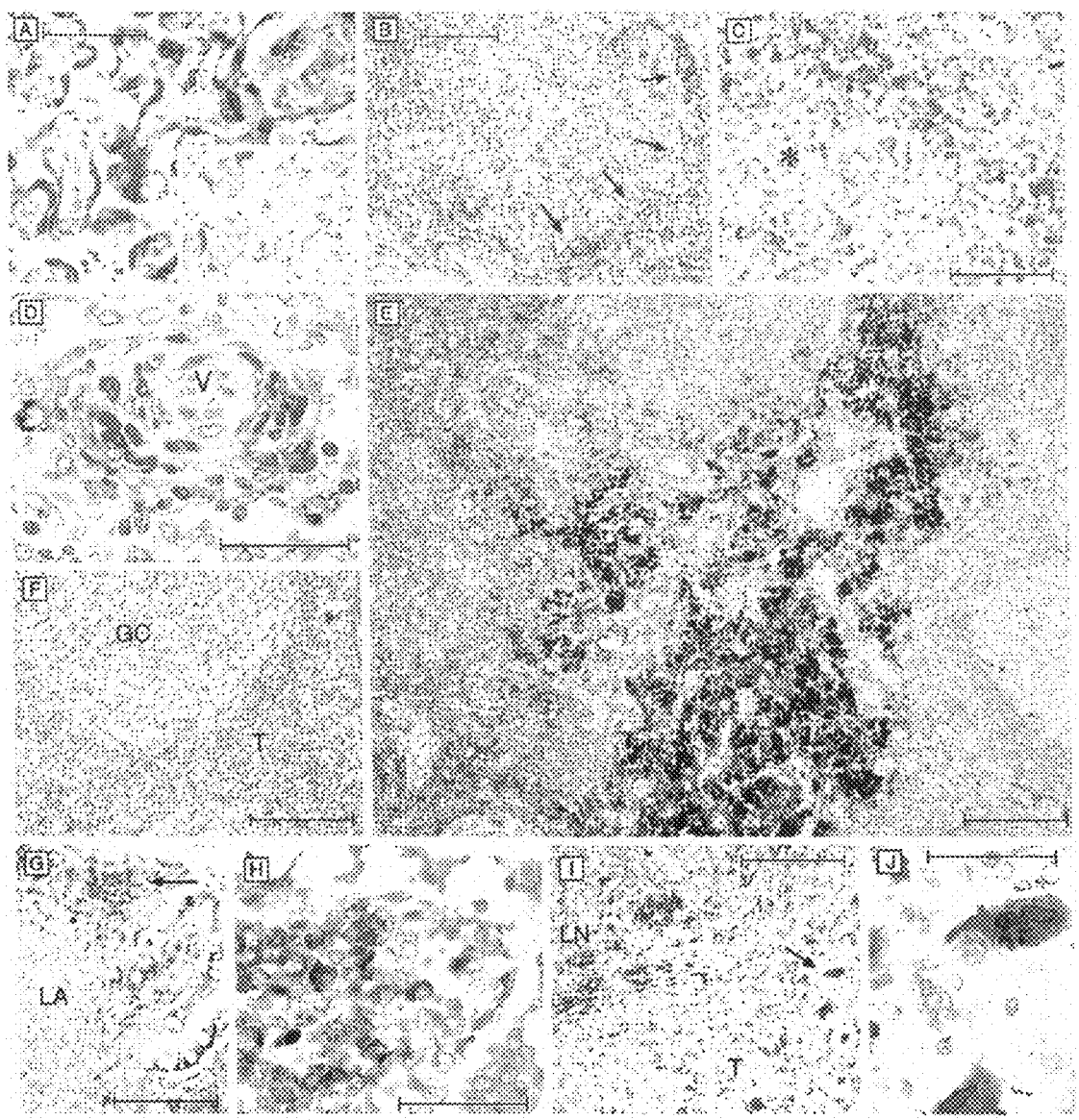
FIG. 8 shows detection of IDO-expressing (IDO$^+$) CD123$^+$ dendritic cells in human tumors and draining lymph nodes in accordance with an embodiment of the present invention. Panel (A) shows a positive control for IDO (brown) in syncytiotrophoblast cells of term human placenta (inset: the same tissue, but with anti-IDO antibody neutralized by an excess of the immunizing peptide and shown at half scale). Panel (B) shows a malignant melanoma primary cutaneous tumor stained for IDO (arrows) (Fast Red chromogen). Panel (C) shows a draining lymph node of a malignant melanoma, showing accumulation of IDO-expressing cells (red) in the lymphoid and perivascular regions of the node, but sparing the macrophage-rich sinuses (asterisk). Panel (D) shows a higher magnification of panel (C), with a characteristic collection of IDO-expressing cells (dark signal) around a high-endothelial venule (V). Panel (E) shows a low-power view of a draining lymph node containing heavily pigmented metastatic melanoma cells (endogenous melanin, black; darkest signal), with confluent infiltration of IDO-expressing cell (red; next darkest signal) around the tumor deposits. Panel (F) shows normal lymphoid tissue with scattered IDO$^+$ cells (red; scattered dark signals) in a germinal center (GC) and T cell regions (T) of a human pharyngeal tonsil from a routine tonsillectomy. Panels (G) and (H) (higher magnification of the region in panel (G) indicated by the arrow) shows co-localization of cells expressing IDO (brown; darkest cytoplasmic signal) and mip-3α (red; next darkest cytoplasmic signal) in the lamina propria of the small intestine, particularly in the subepithelial areas overlying mucosal lymphoid aggregates (LA). Panels (I) and (J) (higher magnification of the region in panel (I) indicated by the arrow) shows expression of mip-3α (red) by tumor cells in a lesion of malignant melanoma metastatic to lymph node, such that the mip-3α$^+$ cells are scattered throughout the tumor (arrow) (T), while the IDO$^+$ (brown) cells are congregated at the margins of the metastasis but confined to the residual lymph node tissue (LN).

For example, malignant melanoma is a tumor with well-defined T cell antigens but which nevertheless is not eliminated by the immune system. In tumor specimens comprising both primary and metastatic lesions, a majority show infiltration of IDO$^+$ cells (FIG. 8B). In addition, recruitment of IDO$^+$ dendritic cells is also seen in carcinoma of the breast, lung, colon and pancreas. Accumulation of these cells occurs primarily around the margins of the tumor and infiltrating along the fibrous stoma, or along the vessels in perivascular cuffs and are not a normal constituent of skin or connective tissue.

Figure 9:
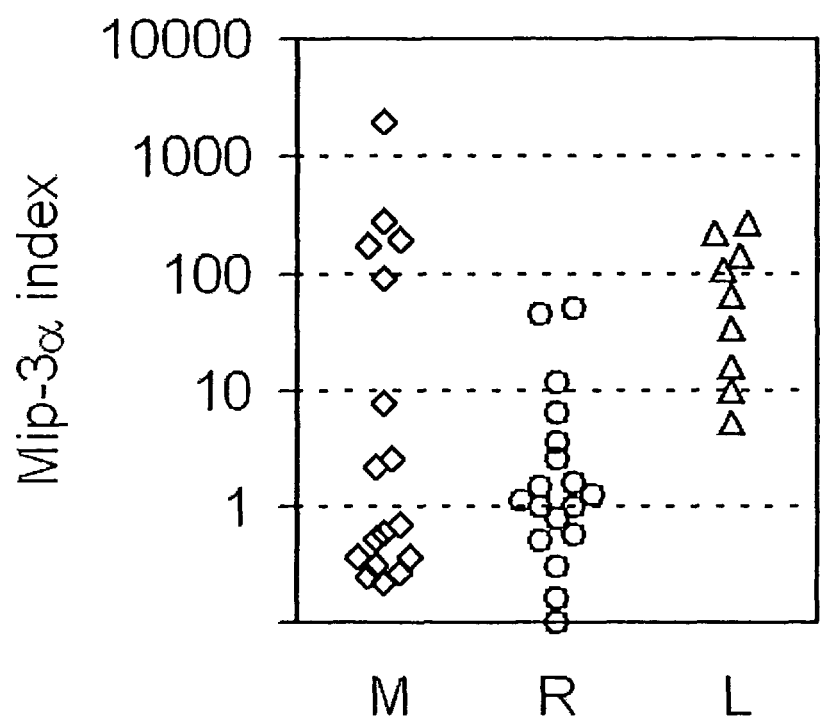
FIG. 9 shows expression of mip-3α mRNA by human tumors in accordance with an embodiment of the present invention. RNA from melanomas (M, n=18), renal cell carcinomas (R, n=19) or non-small cell lung cancers (L, n=9) was analyzed for expression of mip-3α by quantitative PCR calculated as the ratio of mip-3α to the GAPDH housekeeping gene in each sample.

Tumor-draining lymph nodes may be a critical site for initiation of anti-tumor immune responses (Ochsenbein, A. F., et al., *Nature* 411: 1058-1064 (2001)). In an analysis of over 300 tumor-draining lymph nodes from 26 patients with malignant melanoma, markedly abnormal accumulation of IDO$^+$ cells is seen (FIG. 8C-E). The IDO$^+$ cells are found to extensively infiltrate the lymphoid regions of the lymph nodes, largely concentrating in the interfollicular and T cell zones. There is also frequent accumulation around blood vessels (FIG. 8D) and accumulation at the interface between lymphoid tissue and tumor metastases or medullary sinuses (FIG. 8E). Normal lymphoid tissue (tonsillectomy specimens with minimal hypertrophy, or lymph node dissections from patients with early-stage node-negative breast cancer) show only scattered IDO$^+$ cells (FIG. 8F), and do not display the extensive focal collections and confluent areas of IDO$^+$ cells seen in tumor-draining nodes. Also, many primary and metastatic tumors contain individual tumor cells (FIG. 8I) or entire localized regions within the tumor that express mip-3α by immunohistochemistry. Quantitative analysis of mip-3α mRNA by real-time PCR confirms mip3α expression in samples of malignant melanoma (M), renal carcinoma (R), and non-small cell lung cancer (L) (FIG. 9).

Thus, the present invention identifies IDO$^+$ myeloid dendritic cells as a novel immunoregulatory subset of human APCs. The IDO$^+$ dendritic cell population appears to be distinct from the previously described "plasmacytoid" or pre-DC2 dendritic cells (Liu, Y. J., *Cell* 106, 259-262 (2001)). Thus, pre-DC2 express CD123 do not express CD11c, whereas CD11c is found on essentially all IDO$^+$ cells in vitro. In addition, while it is possible that that pre-DC2 cells may express IDO in some situations, the majority of IDO-expressing cells appear to be myeloid-derived.

The present invention differs from previous application of tolerogenic DCs in that: (1) mature DCs which are more effective than immature DCs at suppressing T cells are used; (2) a relatively pure preparation of tolerogenic cells (i.e. expressing IDO) is used, rather than a preparation contaminated by non-tolerogenic (IDO$^{LO}$) cells; and (3) APCs of a type other than DCs may be employed, where the non-dendritic APCs are selected based on expression of IDO. Thus, in an embodiment, the isolated tolerogenic APCs comprise mature dendritic cells cultured under conditions optimized to yield a preparation of IDO$^+$ cells or mature cells enriched for IDO$^+$ cells by selection of IDO$^+$ cells from a mixed population of IDO$^+$/IDO$^{LO}$ cells. Selection of IDO$^+$ cells may take advantage of differential expression of cell surface antigens by either the IDO$^+$ or the IDO$^{LO}$ cells. Thus, cells may be separated by immunosorting, differential adherence or other methods known in the art.

The present invention differs from previous application of immunizing (non-tolerogenic) DCs in that: (a) a relatively pure preparation of non-tolerogenic cells (i.e. not expressing immunosuppressive levels of IDO) is used, rather than a preparation contaminated by tolerogenic (IDO$^+$) cells; and (2) APCs of a type other than DCs may be employed, where the non-dendritic APCs are selected based on low or negative expression of IDO. Thus, in an embodiment, the isolated non-tolerogenic APCs comprise mature dendritic cells cultured under conditions optimized to yield a preparation of $IDO^{LO}$ cells, or mature cells enriched for $IDO^{LO}$ cells by selection of $IDO^{LO}$ cells from a mixed population of $IDO^+$/$IDO^{LO}$ cells. Selection of $IDO^{LO}$ cells may take advantage of differential expression of cell surface antigens by either $IDO^{LO}$ or $IDO^+$ cells. Thus, cells may be separated by immunosorting, differential adherence or other methods known in the art. In another embodiment, the isolated non-tolerogenic APCs comprise mature non-dendritic APCs cultured under conditions optimized to yield a preparation of $IDO^{LO}$ cells, with or without further enrichment by selection of $IDO^{LO}$ cells from a mixed population of $IDO+/IDO^{LO}$ cells.

The present invention teaches that IDO-expressing APCs cells are tolerogenic, and are found in large numbers in tumors and draining lymph nodes. One mechanism contributing to the accumulation of these cells may be tumor-derived mip-3α. Mip-3α is the only known ligand for CCR6, and CCR6 appears to selectively associate with the $IDO^+$ dendritic cell phenotype in vitro. The ability to isolate these $IDO^+$ and $IDO^{LO}$ APCs in vitro provides a means to use specific subsets of the IDO expressing monocytes as therapeutics to either increase or decrease immunologic tolerance.

EXAMPLES

Example 1

Cell Culture

Human monocytes and lymphocytes were isolated as separate fractions by leukocytapheresis and counterflow elutriation (D. H. Munn et al., *J. Exp. Med.* 189, 1363-1372 (1999)). Monocytes (typically >95% purity) were cultured in 100 mm tissue culture petri dishes in RPMI-1640 medium with 10% newborn calf serum (Hyclone) and including penicillin/streptomycin and glutamine. Cultures received either MCSF (200 U/ml, Genetics Institute) on day 0, or GMCSF (50 ng/ml, R&D Systems) +IL4 (50 ng/ml, R&D Systems) on days 0, 2 and 4. For experiments where CCR6 expression was of interest, cultures received a single dose of GMCSF+IL4 (100 ng/ml each) on day 0, with no further supplementation. Loosely adherent dendritic cells (GMCSF+IL4) were harvested by gentle aspiration; adherent macrophages (MCSF) and non-dendritic APCs (GMCSF+IL4) were harvested with EDTA. Other cultures were conducted in serum-free medium (X-vivo 15; BioWhitaker, Walkersville, Md.) plus cytokines.

Example 2

Production of Antibodies

All antibodies were obtained commercially except for polyclonal antiserum against human IDO which was manufactured as a work for hire by ZCB Inc., Hopkinton, Mass. All commercial antibodies and reagents were from BD Biosciences-Pharmingen (San Jose, Calif.) unless specified otherwise. For detection of cell surface antigens, DCs were triple-stained with anti-CD123-biotin (clone 7G3; it was found that clone 9F5 gave suboptimal results with dendritic cells) followed by streptavidin-perCP, plus anti-CD11c-allophycocyanin (clone S-HCL-3) or anti-CCR6-fluorescein (clone 53103.111, R&D systems, Minneapolis, Minn.). CCR6 results were also confirmed using a second anti-CCR6 antibody (clone 11A9; Pharmingen). For detection of IDO, cells were fixed and permeablized (Cytofix/Cytoperm), and then stained with rabbit anti-IDO antibody prepared against the peptide followed by polyerythrin-labeled anti-rabbit secondary antibody (Jackson Immunoresearch, West Grove Pa.) cross-adsorbed against mouse, human and bovine IgG, for multiple labeling). Dendritic cells were gated on forward and side scatter to exclude contaminating lymphocytes and debris.

For preparation of rabbit anti-IDO antibody, the peptide DLIESGQLRERVEKLNMLC (SEQ ID NO: 1) was prepared based on the GenBank sequence of human IDO (M34455) and conjugated to keyhole limpet cyanogen. Rabbits were immunized with conjugated peptide in Freund's adjuvant (all immunization, antibody preparation and affinity purification steps were performed as a work for hire (QCB, Inc., Hopkinton, Mass.). This peptide gave the best results out of several different sequences screened for their ability to detect human IDO in formalin-fixed paraffin-embedded tissue and by flow cytometry. Validation studies showed that this antibody immunoprecipitated the expected 45 kD band from cell lysates, correlated with IDO mRNA and functional enzymatic activity in vitro, identified an interferon-γ-inducible antigen in two known-positive cell lines (THP-1 and HeLa), and detected an antigen by immunohistochemistry which was specifically localized to cells with known expression of IDO (the syncytiotrophoblast cells of human placenta; Y. Kudo and C. A. Boyd, *Biochem. Biophys. Acta* 1500, 119-124 (2000)). Results were consistent from animal to animal, and from lot to lot of antibody.

Example 3

Regulation of IDO Expression during DC Maturation

In humans DCs, maturation has been associated with loss of tolerogenic activity (Dhodapkar, M. V., et al., *J. Exp. Med.*, 193: 233-238 (2001)). The experiments described in FIG. 4 addressed the issue of whether DC maturation down-regulates IDO mediated suppressor activity. Monocyte-derived DCs were cultured for 7 days in X-vivo 15 medium with GMCSF+IL4 (non-adherent cell population, >95% $IDO^+$, >95% $CD123^+$). During the final two days, the cells were either (A) left as immature DCs (no additions); (B) matured using a cytokine cocktail comprising TNFα, IL1β, IL6 and PGE2 (Jonuleit, H. et al., *Eur. J. Immunol.*, 27: 3135-3142 (1997)); or (C) matured using monocyte-conditioned medium (Reddy, A., et al., *Blood* 90: 3640-3546 (1997)). Each group was harvested and added to $5\times10^5$ allogeneic T cells in V-bottom 96 well microtiter wells in 200 µl medium (10% fetal calf serum in RPMI)). Differing numbers of DCs were added to a fixed number of T cells to produce the T cell to APC ratios shown (thus, the greater number of APCs are on the left of the axis, the lesser numbers on the right). Replicate groups of wells received either 200 µM 1-methyl-(D)-tyrptophan (1-MT) (□), or saline control (Δ), to disclose IDO-mediated suppression (defined as the amount of proliferation restored at each T cell:APC ratio by adding 1-MT and shown for one point as an arrow in panel B). After 5 days, T cell proliferation was measured as the incorporation of tritiated thymidine (Munn, D. H. et al., *J. Exp. Med.*, 189: 1363-1372 (1 999).

FIG. 4A shows that higher numbers of immature dendritic cells (lower APC: T cell ratios) were associated with increased IDO mediated suppression (shown as the reduced T cell proliferation at the lower T cell:APC cell ratios, and as enhancement of proliferation when 1-methyl-(D)-tryptophan was added). In FIGS. 4B and 4C, the DCs were matured. It can be seen that the mature DCs show greater IDO mediated suppression (with suppression occurring at T cell: APC cell ratios as low as 100:1). Although the mature DCs were highly suppressive due to the presence of IDO, the mature forms actually function better as antigen-presenting cells compared to the immature form, as revealed by the higher T cell proliferation achieved when suppression was prevented by 1-MT (i.e. the difference between □ and Δ for each experiment). Thus, mature DCs derived under conditions optimized in accordance with the invention were both more suppressive and more effective as APCs than immature DCs. Both of these attributes are desirable for induction of tolerance.

Example 4

Co-expression of IDO with Cell Surface Markers CD123, CC11c and CCR6 in Myeloid APCs Expression of IDO in immature monocyte-derived (myeloid) dendritic cells (Dhodapkar, M. V., et al., *J. Exp. Med.* 193: 233-238 (2001)) and in immunosuppressive monocyte-derived macrophages (Munn, D. H., et al., *J. Exp. Med.* 189: 1363-1372 (1999)) was analyzed. FIG. 5 shows the expression of IDO and CCR6 by myeloid antigen-presenting cells which express the cell surface antigen CD123 (CD123$^+$). Human monocytes were cultured as described above (Example 1) for 7 days with GMCSF+IL4 to produce myeloid dendritic cells (FIGS. 5A and 5C), or for 7 days in MCSF to produce macrophages (FIG. 5B) (Munn, D. H., et al., *J. Exp. Med.* 189: 1363-1372 (1999)). Prior to analysis, cells were treated with interferon-γ (INFγ) for 18 hrs to induce maximal expression of IDO. Harvested cells were triple-stained for CD123, CD11c and IDO. For FIG. 5D, cells were cultured as in Example 1 except in a commercial, FDA-approved serum-free medium formulation (X-vivo 15; BioWhitaker, Waldersville, Md.).

As shown in FIGS. 5A and B, both preparations contained a discrete subset of cells that expressed IDO following interferon-γ treatment. Characterization of these IDO$^+$ cells showed that they all expressed the myeloid-lineage marker CD11c, and CD123, wherein >90% of the IDO$^+$ expressed the myeloid-lineage marker CD11c and >99% of the IDO$^+$ cells expressed CD123. To test whether these were truly DCs, additional phenotyping was performed. Cells were matured with TNFα during the last 2 days of culture, in order to upregulate maturation and costimulatory markers, and non-adherent cells were harvested. Following TNFα, all non-adherent cells displayed a veiled/dendritic morphology. Three-color phenotyping showed that the CD123$^+$/IDO$^+$ subset of cells were uniformly CD14$^-$ and CD83$^+$, consistent with their identity as dendritic cells; uniformly CD11b$^+$ and BDCA-2$^-$ (Dzionek, A., et al., *J. Immunol,* 165: 6037-6046 (2000)) consistent with their myeloid origin, and distinguishing them from plasmacytoid DCs (Grouard, G., et al., *J. Exp. Med.,* 185: 1101-1111 (1997)); and 100% positive for CD80, CD86 and MHC class II (HLA-DR). Under these conditions (bovine serum-based medium) CD11c expression was high on the CD123$^+$ subset, and was lower and variable on the CD123$^{LO}$ subset.

In addition, when monocytes were cultured under conditions that favored expression of CCR6 (serum-free medium, single-dose GMCSF+IL4), the CD123$^+$/IDO$^+$ cells were almost all (>99%) CCR6$^+$ (FIG. 5C). For experiments where CCR6 expression was of interest, cultures received a single dose of GMCSF+IL4 (100 ng/ml each) on day 0, with no further supplementation. Moreover, within the myeloid dendritic cell population, IDO and CCR6 expression were coincident. T and B cells, which also express CCR6, were excluded from analysis by forward and side scatter properties during flow cytometric analysis. The cell-surface CCR6 on these cells was functional: when immature dendritic cells containing a mixture of CCR6-positive and -negative cells were placed in chemotaxis chambers, the CCR6-positive cells selectively migrated in response to a mip3α gradient (data not shown).

Expression of IDO is not found in all types of dendritic cells. Analysis of plasmacytoid dendritic cells, defined as the population of peripheral blood mononuclear cells expressing CD123 but negative for lineage-specific markers (Lin-1 marker cocktail, BD-Pharmingen), revealed no detectable expression of IDO following activation for 6 hrs or 24 hrs with interferon-γ, in the presence of IL3 to support viability (data not shown). Moreover, when the adherent cells (comprising the non-dendritic APC population) from cultures of peripheral blood mononuclear cells in GMCSF+IL4 were examined, they were found to express very low levels of IDO and little CD123 (FIG. 5D). Additional phenotyping of the non-dendritic APCs showed that they were uniformly CD14-positive and CD83-negative (thus, distinguishing them unambiguously from mature dendritic cells, but were >95% positive for CD80 and CD86 (thus, identifying them as mature antigen-presenting cells), and expressed high levels of the MHC class II antigen HLA-DR (further distinguishing them from immature dendritic cells, and identifying them as mature APCs). Consistent with the observed absence of IDO expression, these non-dendritic APCs showed excellent APC function without any detectable IDO-mediated suppression (i.e. no increase in proliferation in the presence of 1-methyl-(D)-typtophan (1-MT) (FIG. 5E), where stippled bars are standard MLR and striped bars are the MLR with 1-MT. The T cell: APC ratio in FIG. 5E was the same (20:1) for both DCs and non-dendritic APCs and both populations were isolated from the same culture of mononuclear cells in GMCSF+IL4 and tested against the same population of T cells in parallel MLRs.

Example 5

Suppression of Allogeneic T Cell Proliferation by Dendritic Cells Expressing IDO The experiments shown in the previous example demonstrated that distinct IDO$^+$ and IDO$^{LO}$ subsets can exist in the same preparation of dendritic cells. This example shows that IDO expressing dendritic cells from such a mixture suppress allogeneic T cell proliferation (FIG. 6).

Myeloid dendritic cells (derived in bovine serum-based medium as in FIG. 5A) were activated for 24 hrs with TNFα (10 ng/ml, BD), labeled with anti-CD123 antibody, then enriched by sorting with goat anti-mouse secondary antibody conjugated to magnetic beads (Miltenyi Biotec). Since expression of cell-surface CD123 correlated closely with possession of inducible IDO, immunomagnetic sorting based on CD123 was used to enrich for the IDO$^+$ subset. Cells selected as CD123$^+$ cells (85-90% purity) by immunomagnetic sorting were then tested as stimulators in an allogeneic MLR. Dot-plots show analysis before ("Pre-sort") and after ("CD123$^+$") enrichment (FIG. 6A).

The CD123$^+$-enriched cells were used as APCs in an allogeneic MLR. Dendritic cells were mixed with purified allogeneic lymphocytes (<1% monocytes, 80-85% T cells, with the balance being B and natural killer (NK) cells) at a 1:10 ratio in V-bottom culture wells. After 5 days, proliferation was measured by 4 hr thymidine incorporation assay. Controls shown include the unfractionated population ("Presort") and the cells remaining after positive selection for CD123 ("Depleted"). Typically <10% of the "Depleted" cell population was CD123$^+$. Solid bars show conventional MLR; open bars show MLR in the presence of 200 uM 1-methyl-(D,L)-tryptophan (1-MT) (Sigma-Aldrich, St. Louis, Mo.), an inhibitor of IDO. In a similar set of experiments, 3 different pairs of donors, each allogeneic to the other, and each pair pre-tested to produce an active MLR were used without 1-MT (solid bars) or with 1-MT (open bars) (FIG. 6C).

As shown in FIGS. 6B and C, the CD123-enriched (CD123$^+$) IDO$^+$ cells were markedly less efficient at stimulating T cell proliferation than either the original unfractionated mixture, or than the CD123-depleted IDO$^{LO}$ subset that remained after sorting. To test the hypothesis that this lack of proliferation was due to active suppression by IDO, cultures were treated with 1-methyl-(D,L)-tryptophan (1-MT), a pharmacologic inhibitor of IDO. In the presence of 1-methyl-(D,L)-tryptophan, the CD123$^+$ dendritic cells stimulated proliferation at or near control levels (FIGS. 6B and C), demonstrating that IDO causes suppression.

Example 6

Figure 7:
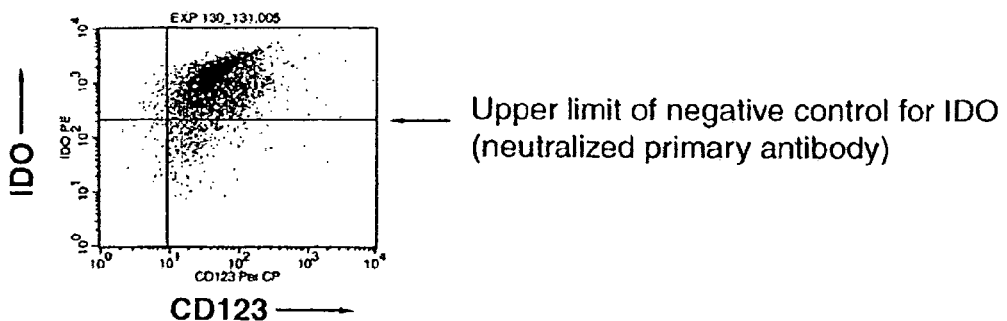
FIG. 7 shows that sorting to generate a population of cells enriched for CD123 expression (CD123$^+$) by immunosorting results in APCs are enriched for cells having high levels of IDO expression (IDO$^+$ APCs) in accordance with an embodiment of the present invention.
Figure 7:
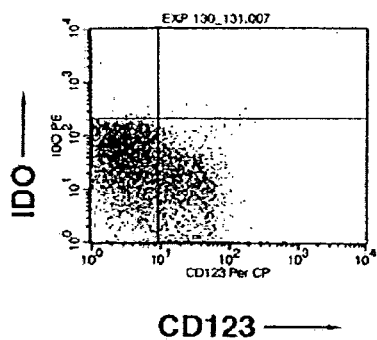

Sorting on the Basis of Cell Surface CD123+ Results in Enrichment of the IDO+ Population This example shows that sorting dendritic cells to select for CD123$^+$ cells results in a population of cells which exhibits high levels of IDO expression. In this experiment, monocyte derived dendritic cells (DCs) were labeled with anti-CD123 antibody and selected using immunomagnetic sorting. Immediately after sorting, cells were dual-stained for CD123 (surface) and IDO (intracellular). As seen in FIG. 7, the positively selected cells were approximately 90% CD123$^+$. In addition, all (>99%) of the cells showed high levels of IDO as detected by staining. In contrast, the residual cells following CD123 depletion were mostly CD123 negative, and expressed low, or undetectable levels of IDO. Thus, it was found that the CD123 depleted population had 10-100 fold lower levels of IDO than the CD123$^+$ population (FIG. 7).

Example 7

Detection of IDO-Expressing CD123$^+$ Dendritic Cells in Human Tumors and Draining Lymph Nodes This example shows that CD123$^+$ dendritic are associated with human tumors and draining lymph nodes. Samples of tumor and tumor-draining lymph nodes were chosen from patients with malignant melanoma, a tumor with well-defined T cell antigens but which nevertheless is not eliminated by the immune system. Recruitment of IDO$^+$ dendritic cells was also seen in carcinoma of the breast, lung, colon and pancreas, tumors which account for almost half of all cancer deaths in the United States.

Archival pathology specimens were stained for expression of IDO and other antigens by immunohistochemistry. Paraffin sections (5 um) were deparaffinized, treated for 8 min with proteinase K (Dako, Carpinteria, Calif.), and stained with rabbit anti-human IDO antibody (5 μg/ml in Tris buffered saline with 0.05% Tween-20 and 10% goat serum). Detection was via secondary antibody conjugated to alkaline phosphatase (LSAB-rabbit kit, Dako) with Fast Red chromogen, or horseradish peroxidase (LSAB2, Dako) and diaminobenzidine. Negative controls consisted of the anti-IDO antibody neutralized with a 100-fold molar excess of the immunizing peptide. Mip-3α (goat polyclonal, R&D Systems) was used following antigen retrieval with citrate (Target, Dako). For dual-staining, the first antibody was applied following appropriate antigen retrieval and detected with peroxidase/diaminobenzidine. Stained slides were then subjected to additional antigen retrieval if required and stained for the second antigen by alkaline phosphatase/Fast Red. Secondary antibodies were cross-adsorbed against mouse, human and bovine IgG for multiple labeling.

In all of these studies, the IDO$^+$ cells observed appeared to be of the same cell type, displaying a characteristic morphology resembling plasmacytoid DCs (Cella, M., et al., *Nature Medicine* 5: 919-923 (1999)); Grouard, G., et al., *J. Exp. Med.*, 185: 1101-1111 (1997); Facchetti, F., et al., *J. Pathol.*, 158: 57-65 (1989)). They were neither histiocytic (macrophage-like) nor classically dendritic in appearance, and did not mark with Ham56 (a macrophage marker) or S100 (a marker of classical dendritic cells) (data not shown). Shown in FIG. 8A is a known positive control for detection of IDO (brown, diaminobenzidine chromogen) in syncytiotrophoblast cells of term human placenta (Kudo, Y., et al., *Biochem. Biophys. Acta* 1500: 119-124 (2000)). The inset shows the same tissue, but with anti-IDO antibody neutralized by an excess of the immunizing peptide. (Bar=100 um, inset at half-scale).

For normal lymphoid tissue controls, non-inflamed tonsil (from routine tonsillectomy, pathologic diagnosis of "hypertrophy") and lymph nodes from patients with node-negative breast cancer who never developed metastases or recurred in 5 years following resection were used. Although not technically "normal," these specimens were the least inflamed lymphoid tissue removed in routine clinical practice. Over 20 of these specimens have been examined, and they consistently show only rare, scattered IDO$^+$ cells, usually localized to germinal centers (FIG. 8F).

For tumor-draining lymph nodes from regional lymph node dissections in patients with a variety of solid tumors (breast, colon, lung, and pancreatic carcinoma, and malignant melanoma) were used. Most of these nodes were not mapped by lymphoscintigraphy, so not all would actually drain the tumor, but many would. In all 5 types of tumor examined, approximately one-third to one-half of patients had one or more lymph nodes showing markedly abnormal collections of IDO$^+$ cells (FIG. 8C). In these nodes, often massive infiltrates of IDO$^+$ cells were localized to the perifollicular and interfollicular areas, often adjacent to the medullary sinuses, or collected in dense perivascular cuffs around high endothelial venules (FIG. 8D). In 328 lymph nodes from 26 patients with melanoma, abnormal infiltration of IDO$^+$ cells was found in 14/26 patients. Where micro-metastases to lymph nodes were present, IDO$^+$ cells often surrounded the margins of the tumor collections (FIG. 8E).

Thus, FIG. 8C shows a draining lymph node of a malignant melanoma showing accumulation of IDO-expressing cells (red) in the lymphoid and perivascular regions of the node, but sparing the macrophage-rich sinuses (asterisk). (Bar=100 um). FIG. 8D shows a higher magnification of panel C, showing a characteristic collection of IDO-expressing cells around a high-endothelial venule (V). (Bar=50 um). FIG. 8E shows a low-power view of a draining lymph node containing heavily pigmented metastatic melanoma cells (endogenous melanin, black; darkest signal), with confluent infiltration of IDO-expressing cells (red; next darkest signal) around the tumor deposits.

For solid tumors, 14 malignant melanoma tumors were examined with 8/14 found to display collections of IDO$^+$ cells at the site of the primary tumor. Usually these were in the connective tissue immediately surrounding the tumor (FIG.

8B, arrows) rather than in the tumor parenchyma itself. Similar infiltrates of IDO+ cells have been seen in breast, lung, and pancreatic tumors.

For inflamed lymphoid tissue tonsils known to be infected (either by clinical diagnosis or by histopathologic diagnosis) and lymph node biopsies bearing the histopathologic diagnosis of "reactive lymph node" were examined. Many of these specimens showed focal or regional collections of IDO+ cells. In tonsils these collections frequently occurred in a subepithelial location beneath the mucosa and along the crypts (not shown).

Finally, gut-associated lymphoid tissue from the (human) small intestine was examined since IDO+ DCs derived in vitro expressed CCR6, and mice with a targeted disruption of CCR6 (Varona, R., et al., J. Clin. Invest., 107: R37-45 (2001)) fail to recruit a population of myeloid DCs into the lymphoid tissue of the gut. FIG. 6G shows prominent collections of IDO+ cells in the lamina propria overlying lymphoid aggregates in the gut, congregating near cells expressing mip-3α (the ligand for CCR6 (Sozzani, S. et al., J. Leukocyte Biol. 66: 1-9 (1999); Zlotnik, A., et al., Immunity 12: 121-127 (2000)).

Thus, it was found that cells expressing IDO (and CCR6) co-localized with cells expressing mip-3α. Sections of normal human small intestine were used as a positive control for mip-3α expression, since murine studies have shown that mip-3α is highly expressed in the subepithelial tissues overlying mucosal lymphoid aggregates of the small intestine (A. Iwasaki and B. L. Kelsall, J. Exp. Med 191: 1381-1394 (2000)). As shown in FIG. 8G, the corresponding region in humans contained focal collections of cells expressing mip-3α, along with extensive co-localization of IDO-expressing dendritic cells to the same areas. Thus, FIGS. 8G and H shows co-localization of cells expressing IDO (brown; darkest cytoplasmic signal) and mip-3α (red; next darkest signal) in the lamina propria of the small intestine, particularly in the subepithelial areas overlying mucosal lymphoid aggregates (LA). FIG. 8H shows a higher magnification of the region in panel G indicated by the arrow. Bar=50 um.

Examination of mip-3α expression in malignancies showed that many primary and metastatic tumors contained individual tumor cells (FIG. 8I) or entire localized regions within the tumor that expressed mip-3α by immunohistochemistry. Although both mip-3α and IDO expressing cells are found in the tumor, they did not appear to be located in identical cells. Thus, FIG. 8I shows expression of mip-3α (red) (arrow, lower right) by tumor cells in a lesion of malignant melanoma metastatic to lymph node. The mip-3α+ cells are scattered throughout the tumor (T), while the IDO+ cells are congregated at the margins of the metastasis but confined to the residual lymph node tissue (LN). FIG. 8J shows a higher magnification of the region in panel M indicated by the arrow, showing mip-3α expression in tumor cells where the bar=50 um.

In addition, the morphology of these cells showed that they were tumor cells, not stroma or other host-derived cells. Quantitative analysis of mip-3α mRNA by real-time PCR confirmed expression in 8/18 samples of malignant melanoma (see Example 8). To ensure that this was not an idiosyncratic property of melanomas, additional RNA samples were analyzed from tumors of unrelated histology and cell of origin (renal cell carcinoma and non-small cell lung cancer). This confirmed that a variety of tumor types express mip-3α (D. Bell et al., J. Exp. Med. 190, 1417-1426 (1999)).

Example 8

Quantification of mip-3α Expression in Human Tumors

It was found that human tumors express mip-3α. RNA was isolated from melanomas (M, n=18), renal cell carcinomas (R, n=19) or non-small cell lung cancers (L, n=9) and analyzed for expression of mip-3α by quantitative RT-PCR (FIG. 9). The RNA was reverse-transcribed using random hexamer priming and analyzed using the LightCycler real-time PCR system (Roche, Indianapolis, Ind.) and FastStart DNA Amplification Kit (SYBR Green 1, Roche). The primers used were: GAPDH (GenBank GI:7669491, sense basepairs (bp) 87-104, antisense bp 289-307) and mip-3α (GenBank GI:4759075, sense bp 103-121, antisense bp410-428). Standard curves were prepared from U937 cells induced with phorbol myristate acetate for 24 hrs, and were linear (r=−0.99) in the range of 100 pg to 100 ng total RNA.

It was found that there was an increase in mip-3α mRNA in all three tumor types assayed (FIG. 9). To permit comparison between different samples the data are presented as an index, calculated as the ratio of mip-3α to the GAPDH housekeeping gene in each sample, normalized to the value of the control cell line (resting U937 cells). The data shown thus represent fold increase of mip-3α expression over that for GAPDH.

The invention has been described in detail with particular reference to preferred embodiments thereof, but it will be understood that variations and modifications can be effected within the spirit and scope of the invention. References cited herein are incorporated in their entirety by reference unless otherwise noted.

What is claimed is:

1. A kit for detecting antigen-presenting cells that express indoleamine-2,3-dioxygenase and CCR6 in a sample of tissue from a tumor or tumor draining lymph node from a subject comprising an antibody to human indoleamine-2,3-dioxygenase and an antibody to human CCR6, wherein each antibody is packaged in at least one individual container.

2. A kit for detecting antigen-presenting cells that express indoleamine-2,3-dioxygenase and CD123 in a sample of tissue from a tumor or tumor draining lymph node from a subject comprising an antibody to human indoleamine-2,3-dioxygenase and an antibody to human CD123, wherein each antibody is packaged in at least one individual container.

3. A kit for detecting antigen-presenting cells that express indoleamine-2,3-dioxygenase and CD1c in a sample of tissue from a tumor or tumor draining lymph node from a subject comprising an antibody to human indoleamine-2,3-dioxygenase and an antibody to human CD11c, wherein each antibody is packaged in at least one individual container.

* * * * *

SEQUENCE LISTING

```
<160> NUMBER OF SEQ ID NOS: 1

<210> SEQ ID NO 1
<211> LENGTH: 19
<212> TYPE: PRT
<213> ORGANISM: Homo sapiens

<400> SEQUENCE: 1

Asp Leu Ile Glu Ser Gly Gln Leu Arg Glu Arg Val Glu Lys Leu Asn
1               5                   10                  15

Met Leu Cys
```